United States Patent [19]
Kobayashi et al.

[11] Patent Number: 5,736,284
[45] Date of Patent: Apr. 7, 1998

[54] CARBAZOLE DERIVATIVE CHARGE TRANSPORTING MATERIAL USING THE SAME AND ELECTROPHOTOGRAPHIC PHOTORECEPTOR

[75] Inventors: Tohru Kobayashi; Yoshimasa Matsushima; Hiroshi Sugiyama; Toshimitsu Hagiwara, all of Kanagawa, Japan

[73] Assignee: Takasago International Corporation, Tokyo, Japan

[21] Appl. No.: 839,594

[22] Filed: Apr. 15, 1997

[30] Foreign Application Priority Data

Apr. 30, 1996 [JP] Japan ............................ 8-130556

[51] Int. Cl.$^6$ ........................ G03G 5/06; C07D 209/82
[52] U.S. Cl. ........................ 430/79; 430/58; 430/59; 430/83; 252/500; 548/440
[58] Field of Search ................ 430/59, 79, 83; 252/500; 548/440

[56] References Cited

U.S. PATENT DOCUMENTS

| | | |
|---|---|---|
| 3,791,826 | 2/1974 | Cherry et al. |
| 4,859,556 | 8/1989 | Sasaki ............................ 430/73 |
| 4,892,949 | 1/1990 | Sasaki ............................ 546/98 |
| 5,159,087 | 10/1992 | Shimada et al. .................. 430/79 |
| 5,567,560 | 10/1996 | Hagiwara et al. ................. 430/59 |
| 5,573,878 | 11/1996 | Hagiwara et al. ................. 430/59 |

FOREIGN PATENT DOCUMENTS

| | | |
|---|---|---|
| 57-165841 | 10/1982 | Japan ............................ 430/79 |
| 58-1477479 | 9/1983 | Japan ............................ 430/79 |
| 61-241762 | 10/1986 | Japan . |
| 63-13047 | 1/1988 | Japan ............................ 430/79 |
| 315853 | 1/1991 | Japan . |
| 542661 | 6/1993 | Japan . |

*Primary Examiner*—Roland Martin
*Attorney, Agent, or Firm*—Sughrue, Mion, Zinn, Macpeak & Seas, PLLC

[57] ABSTRACT

A charge transporting material high in solubility in a binder polymer and having high carrier mobility is disclosed, which contains a carbazole derivative represented by the following general formula (1):

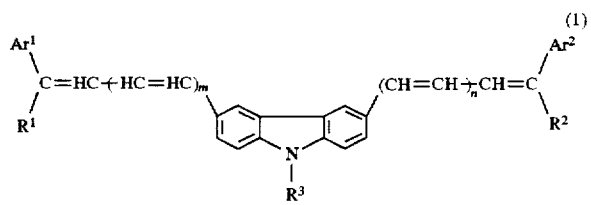

wherein $Ar^1$ and $Ar^2$, which may be the same or different, each represents an aryl group which may have a substituent group; $R^1$ and $R^2$, which may be the same or different, each represents a lower alkyl group or an aryl group which may have a substituent group; $R^3$ represents a lower alkyl group, an alicyclic alkyl group having 5 to 7 carbon atoms, an aryl group which may have a substituent group, or an aralkyl group which may have a substituent group; and m and n each represents an integer of 0 or 1. An electrophotographic photoreceptor containing the charge transporting material is also disclosed.

3 Claims, No Drawings

CARBAZOLE DERIVATIVE CHARGE TRANSPORTING MATERIAL USING THE SAME AND ELECTROPHOTOGRAPHIC PHOTORECEPTOR

FIELD OF THE INVENTION

The present invention relates to a carbazole derivative represented by the following general formula (1), a charge transporting material containing the same, and further an electrophotographic photoreceptor comprising the charge transporting material.

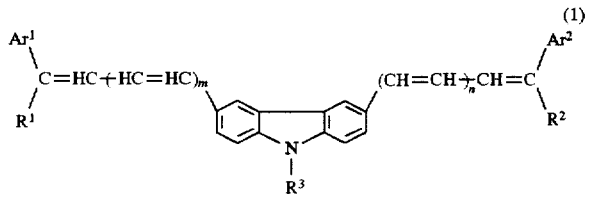

wherein $Ar^1$ and $Ar^2$, which may be the same or different, each represents an aryl group which may have a substituent group; $R^1$ and $R^2$, which may be the same or different, each represents a lower alkyl group or an aryl group which may have a substituent group; $R^3$ represents a lower alkyl group, an alicyclic alkyl group having 5 to 7 carbon atoms, an aryl group which may have a substituent group, or an aralkyl group which may have a substituent group; and m and n each represents an integer of 0 or 1.

BACKGROUND OF THE INVENTION

In recent years, amorphous silicon, amorphous selenium, cadmium sulfide, zinc oxide and the like have been used as inorganic photoconductors. In some cases, however, they are expensive because of difficulty in producing them, or toxic to cause a problem from the viewpoint of the protection of the environment.

On the other hand, as organic photoconductors, particularly, a form in which photoconductors are functionally separated into charge generating materials and charge transporting materials has been actively proposed (for example, U.S. Pat. No. 3,791,826). In this system, materials high in the efficiency of occurrence of carriers (the term "carrier" indicates charge, hereinafter the same) are used as the charge generating materials, and materials high in charge transporting capability are combined as the charge transporting materials, thereby possibly obtaining high-sensitive electrophotographic photoreceptors.

Of these, requirements for the charge transporting materials are efficient receiving of carriers generated in the charge generating materials by light irradiation under application of the electric field, rapid transfer thereof in photoreceptor layers, and rapid disappearance of surface charge. The speed at which the carriers transfer per unit electric field is called carrier mobility. Higher carrier mobility means faster transfer of the carriers in charge transporting layers. This carrier mobility is inherent in the charge transporting materials, and therefore, in order to achieve high carrier mobility, it is necessary to use materials high in carrier mobility. In the present state, however, it can not be said yet that a sufficient level is reached.

Further, when the charge transporting material is used by dissolving it in an organic solvent together with a binder polymer and applying the resulting solution, it is necessary to form an organic thin film with no deposition of crystals or no formation of pinholes in a coated film. This is because application of a high electric field to the resulting thin film causes dielectric breakdown at portions at which microcrystals or pinholes are formed, contributing to noise.

Furthermore, even if both the charge generating material and the charge transporting material are good in characteristics, it is important that carrier injection from the charge generating material to the charge transporting material, namely charge injection from the charge generating layer to the charge transporting layer, is efficiently carried out. This charge injection depends on the characteristics of the interface of the charge generating material (or a charge generating layer) and the charge transporting material (or a charge transporting layer), and is not performed in the same way among various materials. As described above, various conditions are required for the charge transporting materials, so that the charge transporting materials having various characteristics have been developed.

Previously, an α-phenylstilbene derivative represented by the following formula (A) has been proposed as the charge transporting material, for example, in JP-B-2-24864 (the term "JP-B" as used herein means an "examined Japanese patent publication"). This also includes a carbazole derivative such as 3-(2',2'-diphenylvinyl)-9-ethylcarbazole (B) related to the present invention.

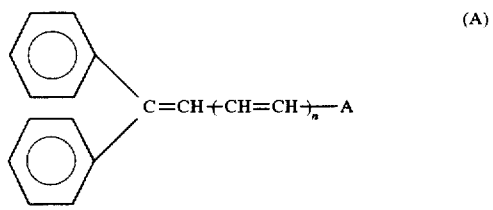

wherein A represents a 9-anthryl group or an N-alkylcarbazolyl group or

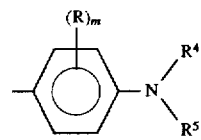

wherein R represents a lower alkyl group, a lower alkoxy group or a halogen atom; $R^4$ and $R^5$ each represents a lower alkyl group, a benzyl group or a phenyl group unsubstituted or substituted by a lower alkyl group, a lower alkoxy group or a halogen atom; m represents an integer of 0 or 1; and n represents an integer of 0 or 1.

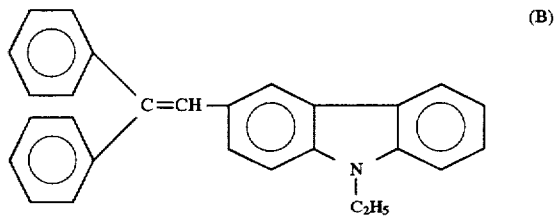

Further, an electrophotographic photoreceptor using a similar carbazole derivative (C) is proposed in JP-A-61-241762 (the term "JP-A" as used herein means an "unexamined published Japanese patent application").

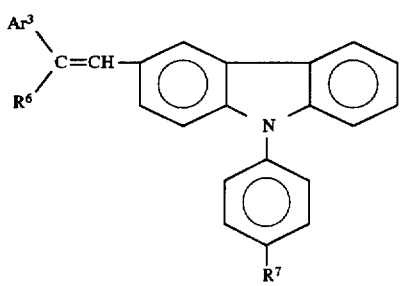

wherein Ar³ represents a substituted or unsubstituted aryl group; R⁶ represents a substituted or unsubstituted alkyl or aryl group; and R⁷ represents a hydrogen atom, a halogen atom, or a substituted or unsubstituted alkyl or alkoxy group.

On the other hand, an electrophotographic photoreceptor containing a bisstyryl type compound represented by general formula (D) as an active ingredient is shown in JP-B-5-42661.

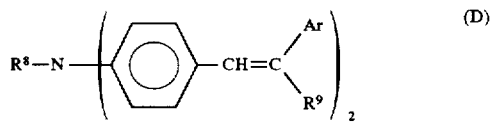

wherein $R^8$ represents an alkyl group including a substituted alkyl group, or an aryl group including a substituted aryl group; $R^9$ represents a hydrogen atom, an alkyl group including a substituted alkyl group, or an aryl group including a substituted aryl group; and Ar represents an aryl group including a substituted aryl group.

In addition, a compound represented by (E) in which a carbazole skeleton has three styryl groups as substituent groups is shown in JP-A-3-15853.

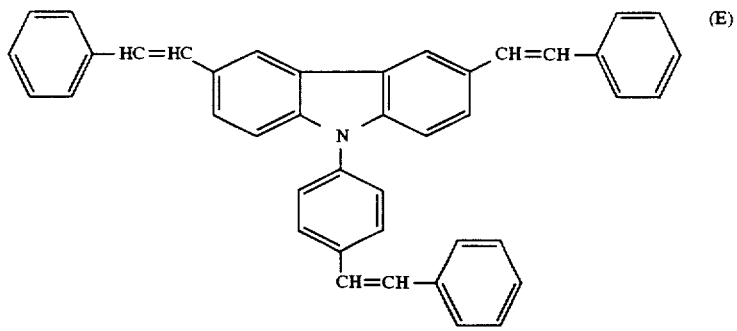

At the present state, however, the carrier mobility of these compounds is not necessarily high, the sensitivity of the electrophotographic photoreceptors using them is not sufficient, and the solubility in binder polymers is also not said to be satisfactory. For the charge transporting materials, the demand therefor has increased more and more, and further new materials which can comply with various conditions have been desired therewith.

Accordingly, the development of new materials has been desired which can satisfy the solubility in binder polymers, are high in carrier mobility, and can exhibit high-sensitive good electrophotographic characteristics.

SUMMARY OF THE INVENTION

An object of the present invention is to provide a new material excellent in various characteristics, such as good solubility in a binder polymer, high carrier mobility when an electrophotographic photoreceptor is formed, and high sensitivity, in a charge transporting material.

At the present state as described above, the present inventors have conducted intensive investigation in various compounds. As a result, the present inventors have discovered that a carbazole derivative represented by the following general formula (1), which has a substituent group of an arylvinyl skeleton or a substituent group of an arylbutadienyl skeleton at each of the 3- and 6-positions of carbazole substituted at the 9-position, can solve the above-mentioned problem, thus completing the invention.

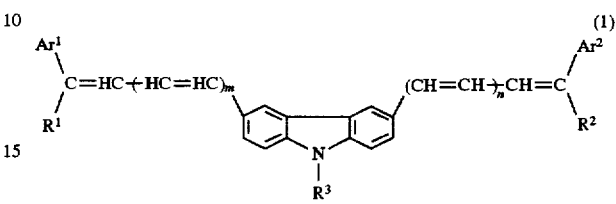

wherein $Ar^1$ and $Ar^2$, which may be the same or different, each represents an aryl group which may have a substituent group; $R^1$ and $R^2$, which may be the same or different, each represents a lower alkyl group or an aryl group which may have a substituent group; $R^3$ represents a lower alkyl group, an alicyclic alkyl group having 5 to 7 carbon atoms, an aryl group which may have a substituent group, or an aralkyl group which may have a substituent group; and m and n each represents an integer of 0 or 1.

That is, the present inventors have discovered that compound (1) is good in solubility in the binder polymer, develops no deposition of crystals or no formation of pinholes, and can exhibit high carrier mobility, and that a photoreceptor using it is high in sensitivity and low in residual potential.

The present invention therefore relates to a novel carbazole derivative represented by the above-mentioned general formula (1), a charge transporting material containing the compound of general formula (1), and an electrophotographic photoreceptor containing said charge transporting material.

DETAILED DESCRIPTION OF THE INVENTION $Ar^1$ and $Ar^2$ of compound (1) of the invention, which may be the same or different, include, for example, lower alkyl group-substituted phenyl groups such as orthotolyl, metatolyl, paratolyl and xylyl groups, alkoxy group-substituted phenyl groups such as methoxyphenyl, ethoxyphenyl and propoxyphenyl groups, halogen-substituted phenyl groups such as chlorophenyl, bromophenyl, fluorophenyl and iodophenyl groups, and amino group-substituted groups such as diarylamino and dialkylamino groups, as well as unsubstituted aryl groups such as phenyl and naphthyl groups. $R^1$ and $R^2$, which may be the same or different, each represents a lower alkyl group or an aryl group which may have a substituent group. The lower alkyl groups include alkyl groups having 1 to 4 carbon atoms, for example, methyl, ethyl, n-propyl, isopropyl, n-butyl, s-butyl and t-butyl groups. The aryl groups which may have substituent groups include a group of substituent groups similar to $Ar^1$ and $Ar^2$ described above.

$R^3$ include alicyclic groups having 5 to 7 carbon atoms, namely cyclopentyl, cyclohexyl and cycloheptyl groups, and further aralkyl groups which may have substituent groups such as benzyl, tolylmethyl, methoxybenzyl and chlorobenzyl groups, as well as lower alkyl groups similar to $R^1$ and $R^2$ described above, and aryl groups which may have substituent groups similar to $Ar^1$ and $Ar^2$ described above.

Further, preferred examples of compound (1) of the present invention include but are not limited to compounds shown in Tables 1 and 2 given below.

TABLE 1

| Exemplified Compound | m | n | $Ar^1$ | $R^1$- | $Ar^2$ | $R^2$ | $R^3$ |
|---|---|---|---|---|---|---|---|
| 1 | 0 | 0 | Ph | Ph | Ph | Ph | Me |
| 2 | 1 | 1 | Ph | Ph | Ph | Ph | Me |
| 3 | 0 | 0 | Ph | Me | Ph | Me | Me |
| 4 | 0 | 0 | Ph | Ph | Ph | Ph | Et |
| 5 | 0 | 0 | Ph | Ph | Ph-(3)Me | Ph-(3)Me | Et |
| 6 | 0 | 1 | Ph | Ph | Ph | Ph | Et |
| 7 | 0 | 0 | Ph | Ph | Ph | 2-Naph | Et |
| 8 | 0 | 0 | Ph-(2)Me(4)Me | Ph-(2)Me(4)Me | Ph-(2)Me(4)Me | Ph-(2)Me(4)Me | Et |
| 9 | 0 | 0 | Ph-(4)Cl | Ph | Ph-(4)Cl | Ph | Et |
| 10 | 1 | 1 | 1-Naph | Ph | 1-Naph | Ph | Et |
| 11 | 1 | 1 | Ph-(4)MeO | Ph | Ph-(4)MeO | Ph | Et |
| 12 | 1 | 1 | Ph | Ph | Ph | Ph | Et |
| 13 | 0 | 0 | Ph | Me | Ph | Me | iPr |
| 14 | 0 | 0 | Ph | Ph | Ph | Ph | iPr |
| 15 | 1 | 1 | Ph | Ph | Ph | Ph | iPr |
| 16 | 1 | 1 | Ph-(4)Me | Ph | Ph-(4)Me | Ph | iPr |
| 17 | 0 | 0 | Ph-(3)Me | Ph-(3)Me | Ph-(3)Me | Ph-(3)Me | iPr |
| 18 | 1 | 1 | Ph-(3)Me | Ph | Ph-(3)Me | Ph | iPr |
| 19 | 0 | 0 | Ph | Ph | Ph | Ph | Ph |
| 20 | 0 | 1 | Ph | Ph | Ph | Ph | Ph |
| 21 | 1 | 1 | Ph | Ph | Ph | Ph | Ph |
| 22 | 0 | 0 | Ph | Ph | Ph | Ph | Ph-(4)Me |
| 23 | 1 | 1 | Ph | Ph | Ph | Ph | Ph-(4)Me |
| 24 | 0 | 0 | Ph | Ph-(3)Me | Ph | Ph-(3)Me | $Ch_2Ph$ |
| 25 | 1 | 1 | Ph-(4)Me | Ph-(4)Me | Ph-(4)Me | Ph-(4)Me | $Ch_2Ph$ |
| 26 | 0 | 0 | Ph | Ph | Ph | Ph | s-Bu |
| 27 | 1 | 1 | Ph | Ph | Ph | Ph | s-Bu |

TABLE 2

| Exemplified Compound | m | n | $Ar^1$ | $R^1$- | $Ar^2$ | $R^2$ | $R^3$ |
|---|---|---|---|---|---|---|---|
| 28 | 0 | 0 | Ph | Ph | Ph | Ph | n-Bu |
| 29 | 1 | 1 | Ph | Ph | Ph | Ph | n-Bu |
| 30 | 0 | 0 | Ph | Me | Ph | Me | n-Bu |
| 31 | 0 | 0 | Ph | Ph | Ph | Ph | n-Pr |
| 32 | 0 | 0 | Ph | Ph | Ph-(3)Me | Ph-(3)Me | n-Pr |
| 33 | 0 | 1 | Ph | Ph | Ph | Ph | n-Pr |
| 34 | 0 | 0 | Ph | Ph | Ph | 2-Naph | n-Pr |
| 35 | 0 | 0 | Ph-(2)Me(4)Me | Ph-(2)Me(4)Me | Ph-(2)Me(4)Me | Ph-(2)Me(4)Me | n-Pr |
| 36 | 0 | 0 | Ph-(4)Cl | Ph | Ph-(4)Cl | Ph | n-Pr |
| 37 | 1 | 1 | 1-Naph | Ph | 1-Naph | Ph | n-Pr |
| 38 | 1 | 1 | Ph-(4)MeO | Ph | Ph-(4)MeO | Ph | n-Pr |
| 39 | 1 | 1 | Ph | Ph | Ph | Ph | n-Pr |
| 40 | 0 | 0 | Ph | Me | Ph | Me | t-Bu |
| 41 | 0 | 0 | Ph | Ph | Ph | Ph | t-Bu |
| 42 | 1 | 1 | Ph | Ph | Ph | Ph | t-Bu |
| 43 | 1 | 1 | Ph-(4)Me | Ph | Ph-(4)Me | Ph | t-Bu |
| 44 | 0 | 0 | Ph-(3)Me | Ph-(3)Me | Ph-(3)Me | Ph-(3)Me | t-Bu |
| 45 | 1 | 1 | Ph-(3)Me | Ph | Ph-(3)Me | Ph | t-Bu |
| 46 | 0 | 0 | Ph | Ph | Ph | Ph | Ph-(4)Br |
| 47 | 0 | 1 | Ph | Ph | Ph | Ph | Ph-(4)Br |
| 48 | 1 | 1 | Ph | Ph | Ph | Ph | Ph-(4)Br |
| 49 | 0 | 0 | Ph | Ph | Ph | Ph | Ph-(3)Me |
| 50 | 1 | 1 | Ph | Ph | Ph | Ph | Ph-(3)Me |
| 51 | 0 | 0 | Ph | Ph-(3)Me | Ph | Ph-(3)Me | Ph-(4)MeO |
| 52 | 1 | 1 | Ph-(4)Me | Ph-(4)Me | Ph-(4)Me | Ph-(4)Me | Ph-(4)MeO |
| 53 | 0 | 0 | Ph | Ph | Ph | Ph | cyclohexyl |
| 54 | 1 | 1 | Ph | Ph | Ph | Ph | cyclohexyl |

The abbreviations used in Tables show the following meanings:

Ph-(4)Me; a phenyl group substituted by a methyl group at the 4-position

Ph-(3)Me; a phenyl group substituted by a methyl group at the 3-position

Ph-(4)Cl; a phenyl group substituted by a chlorine atom group at the 4-position

Ph-(4)Br; a phenyl group substituted by a bromine atom group at the 4-position

Ph-(4)MeO; a phenyl group substituted by a methoxy group at the 4-position

Ph-(2)Me(4)Me; a phenyl group substituted by methyl groups at the 2- and 4-positions 1-Naph; a naphthyl group bonded at the 1-position 2-Naph; a naphthyl group bonded at the 2-position Carbazole derivative (1a) represented by general formula (1) wherein m=n=0, $Ar^1=Ar^2$ and $R^1=R^2$ can be synthesized according to reaction scheme 1:

Reaction Scheme 1

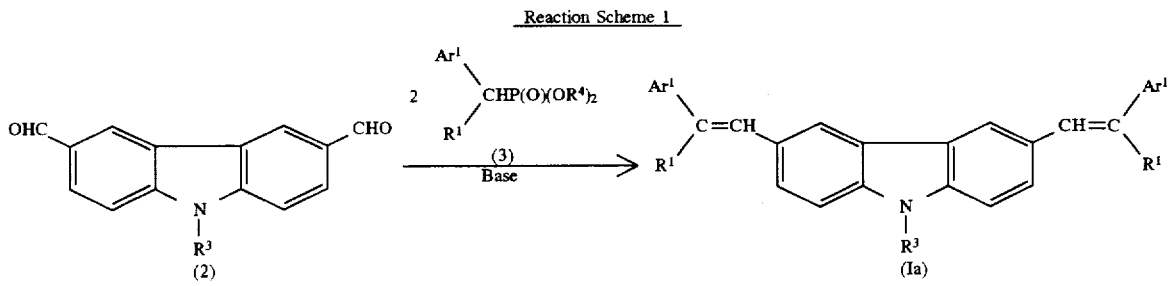

wherein $Ar^1$, $R^1$ and $R^3$ have the same meanings as described above, and $R^4$ represents a lower alkyl group.

$R^4$ represents a methyl group, an ethyl group, a propyl group or a butyl group, and a methyl group or an ethyl group is particularly preferred.

That is, this derivative can be easily produced by allowing 9-position-substituted 3,6-diformylcarbazole (2) to react with a 2-fold molar amount of substituted dialkyl phosphite (3) at a temperature from room temperature to about 80° C. in the presence of a base, for example, by use of the method described in *Jikken Kagaku Koza* (*A Course of Experimental Chemistry*), 4th edition, vol. 19, page 72 (edited by The Chemical Society of Japan, published by Maruzen Co., Ltd.). As the base, sodium hydroxide, sodium amide or a metal alkoxide such as sodium methoxide, sodium t-butoxide or potassium t-butoxide is used, and the molar amount thereof is 1 or more times, preferably 1 to 1.5 times that of substituted dialkyl phosphite (3). Solvents which can be used include lower alcohols such as methanol and ethanol, ethers such as 1,2-dimethoxyethane, diethyl ether, tetrahydrofuran and dioxane, hydrocarbons such as toluene and xylene, aprotic polar solvents such as dimethyl sulfoxide, N,N-dimethylformamide, N,N-dimethylacetamide and N-methylpyrrolidone and mixtures thereof.

Here, 9-position-substituted 3,6-diformylcarbazole (2) can be obtained by conducting the Vielsmeyer-Haak reaction to 9-position-substituted carbazole (4) under the coexistence of Lewis acid or protonic acid (reaction scheme 2). The molar amount of Lewis acid or protonic acid is preferably 1 to 2 times that of 9-position-substituted carbazole (4).

Reaction Scheme 2

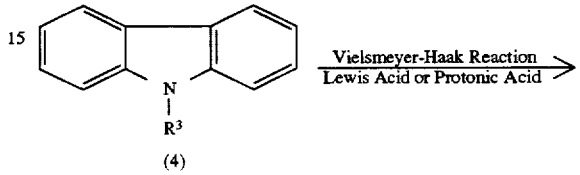

-continued
Reaction Scheme 2

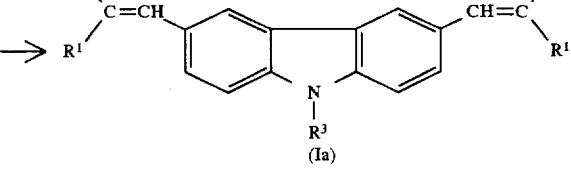

wherein $R^3$ have the same meaning as described above.

Further, substituted dialkyl phosphite (3) is obtained by heating a corresponding aralkyl chloride or bromide and a trialkyl phosphite directly or in a solvent such as toluene or xylene.

On the other hand, carbazole derivative (1b) represented by general formula (1) of the present invention wherein m=n=0, and $Ar^1$ and $Ar^2$, and $R^1$ and $R^2$ may each appropriately be the same or different can be synthesized according to reaction scheme 3:

Reaction Scheme 3

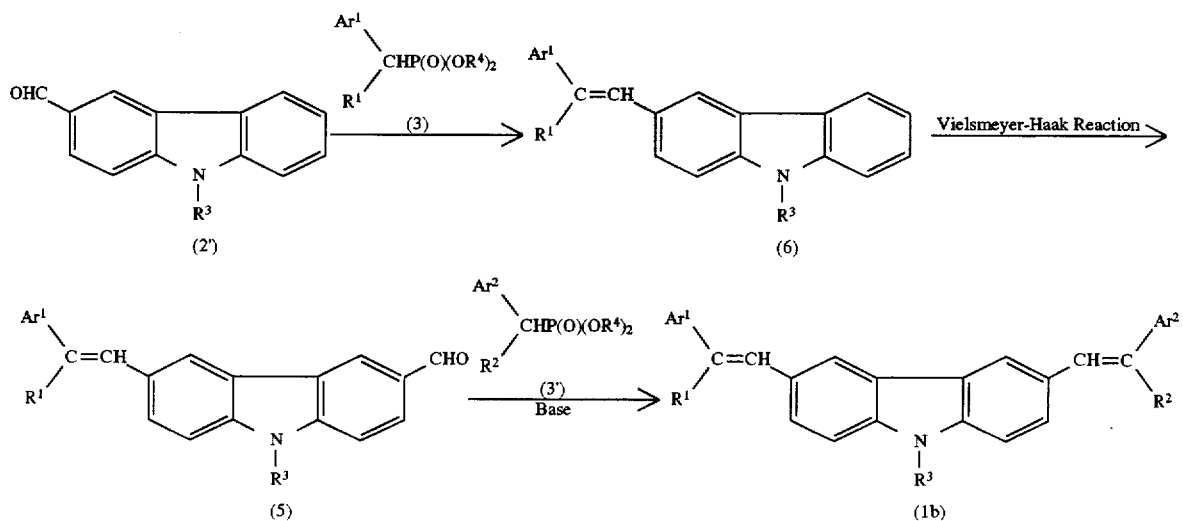

wherein $Ar^1$, $R^1$, $Ar^2$, $R^2$ and $R^3$ have the same meanings as described above, and $R^4$ represents a lower alkyl group.

That is, 9-position-substituted 3-formylcarbazole (2') is allowed to react with an equimolar (1-fold molar) amount of substituted dialkyl phosphite (3) in the presence of a base to synthesize 9-position-substituted 3-vinylcarbazole (6). 9-position-substituted 3-vinyl-6-formylcarbazole (5) is synthesized by the Vielsmeyer-Haak reaction of (6), and a dialkyl phosphite different from dialkyl phosphite (3) used above is allowed to react therewith, thereby being able to synthesize the desired compound (1b) of the present invention.

Further, compound (5) can also be synthesized by allowing 9-position-substituted 3,6-diformylcarbazole (2) to react with an equimolar (1-fold molar) amount of substituted dialkyl phosphite (3) in the presence of a base (reaction scheme 4).

Reaction Scheme 4

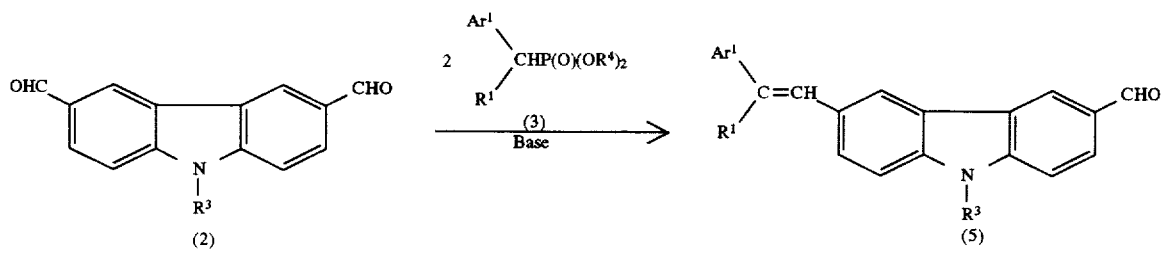

On the other hand, carbazole derivative (1c) represented by general formula (1) of the present invention wherein m=0 and n=1 can be synthesized according to reaction scheme 5.

Reaction Scheme 5

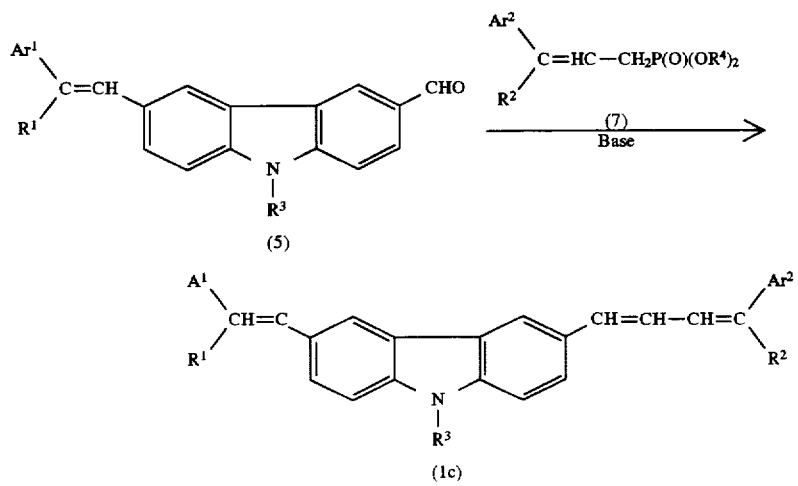

wherein $Ar^1$, $R^1$, $Ar^2$, $R^2$ and $R^3$ have the same meanings as described above, and $R^4$ represents a lower alkyl group.

That is, derivative (1c) can be synthesized by allowing monoformyl compound (5) synthesized according to reaction scheme 3 or 4 described above to react with dialkyl 3-arylallylphosphite (7).

Further, dialkyl 3-arylallylphosphite (7) can be obtained according to reaction scheme 6.

exceptions that ketone derivative (11) is used as a starting material, and that R—MgHal is used in place of methylmagnesium chloride.

Then, arylethylene (9) is allowed to react with paraformaldehyde $(CH_2O)_n$ and hydrogen chloride in acetic acid according to the method described in JP-A-49-75564 to obtain 3-arylallyl chloride (10). Further, the resulting 3-arylallyl chloride (10) is allowed to react with a trialkyl

Reaction Scheme 6

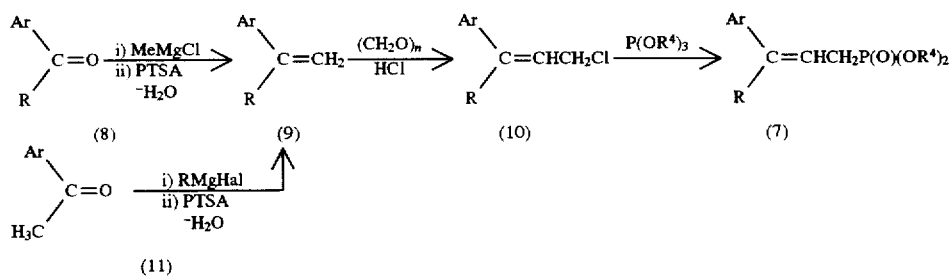

wherein Ar represents $Ar^1$ or $Ar^2$ described above, R represents $R^1$ or $R^2$ described above, and Hal represents a halogen atom.

That is, (i) methylmagnesium chloride (MeMgCl) is allowed to react with carbonyl derivative (8), and (ii) subsequently, the resulting alcohol form is dehydrated in the presence of an acid to obtain arylethylene (9). As the acid, one usually employed in the dehydration reaction, such as PTSA (p-toluenesulfonic acid), can be used.

Here, arylethylene (9) can be obtained by the same reaction as with (i) and (ii) described above, with the phosphite, thereby being able to obtain dialkyl 3-arylallylphosphite (7).

Here, as the trialkyl phosphite, the same one as described in the synthesis of (3) mentioned above can be used.

On the other hand, carbazole derivative (1d) represented by general formula (1) of the present invention wherein m=n=1, $Ar^1$=$Ar^2$ and $R^1$=$R^2$ can be synthesized by allowing 2-fold excess molar amount of dialkyl 3-arylallylphosphite (7) to react with 9-position-substituted 3,6-diformylcarbazole (2), as shown in reaction scheme 7.

Reaction Scheme 7

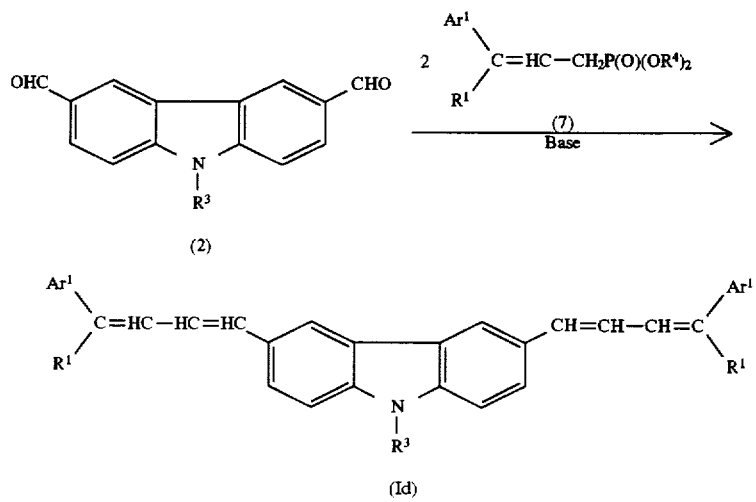

wherein $Ar^1$, $R^1$ and $R^3$ have the same meanings as described above, and $R^4$ represents a lower alkyl group.

Further, carbazole derivative (1e) represented by general formula (1) of the present invention wherein m=n=1, and $Ar^1$ and $Ar^2$, and $R^1$ and $R^2$ may each appropriately be the same or different can be synthesized according to reaction scheme 8:

That is, diformyl form (2) is allowed to react with an equimolar (1-fold molar) amount of dialkyl 3-arylallylphosphite (7) in the presence of a base to synthesize 9-position-substituted 3-(1',3'-butadienyl)-6-formylcarbazole (12), and a dialkyl 3-arylallylphosphite different from (7) used above is allowed to react therewith.

Reaction Scheme 8

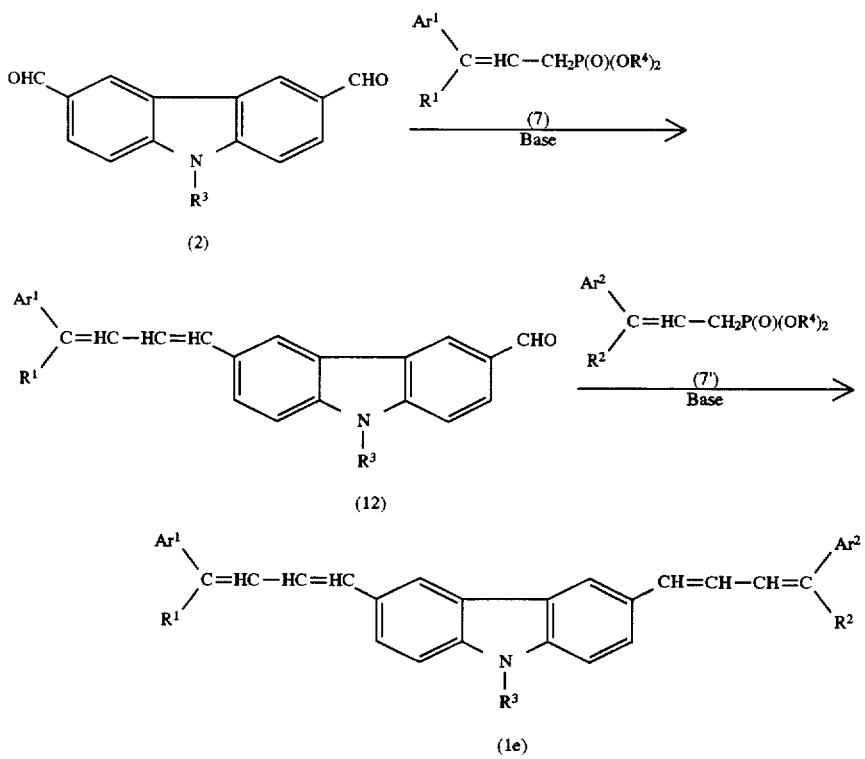

wherein $Ar^1$, $R^1$, $Ar^2$, $R^2$ and $R^3$ have the same meanings as described above, and $R^4$ represents a lower alkyl group.

thereby being able to synthesize the desired compound (1e) of the present invention.

The use of the above-mentioned compound (1) of the present invention as a charge transporting material gives high carrier mobility and permits acquisition of the electrophotographic photoreceptor high in sensitivity.

Further, compound (1) of the present invention can be used in a wide field such as organic electroluminescence (EL).

Specifically, in the electrophotographic photoreceptor of the present invention, compound (1) of the present invention is used as a charge transporting material in a charge transporting layer of a lamination type electrophotographic photoreceptor having a charge generating layer and the charge transporting layer functionally separated on a conductive support.

Further, it can also be utilized as a charge transporting material of a monolayer electrophotographic photoreceptor containing a charge generating material and one or several kinds of charge transporting materials in the same layer.

The charge transporting layer in which compound (1) of the present invention is used as the charge transporting material is formed by vapor-depositing only compound (1) of the present invention as such over the conductive support or the charge generating layer, or by coating the conductive support or the charge generating layer with a solution in which compound (1) of the present invention and a binder are dissolved in an appropriate solvent, followed by drying. On the other hand, the monolayer photoreceptor containing the charge generating agent and compound (1) of the present invention is obtained by coating the conductive support with a solution in which the charge generating agent and compound (1) of the present invention are dissolved or dispersed in an appropriate solvent together with a binder, followed by drying. Further, the monolayer photoreceptor containing compound (1) of the present invention and an electron acceptor type compound which can form a charge transporting complex with compound (1) of the present invention can also be obtained in a similar manner.

Here, the binders include, for example, polycarbonates, polyesters, polystyrene, polyacrylates, polymethacrylates, polyamides, acrylic resins, vinyl chloride resins, vinyl acetate resins, epoxy resins, polyurethanes and copolymers thereof. In addition to such insulating polymers, organic photoconductive polymers such as polyvinylcarbazole, polyvinylanthracene and polyvinylene can also be used.

Of these binders, polycarbonates represented by general formula (F) is preferred. Specifically, bisphenol A type polycarbonates (for example, Yupilon E series manufactured by Mitsubishi Gas Chemical Company, Inc.) represented by formula (G) and bisphenol Z type polycarbonate resins (for example, Polycarbonate Z series manufactured by Mitsubishi Gas Chemical Company, Inc.) represented by formula (H) are particularly preferred. In addition, polycarbonates represented by formulas (I), (J) and (K) can also be used. Copolymers composed of mixtures of monomer units represented by these formula (G) to (K) can also be used. Of these, copolymerized polycarbonates containing biphenol carbonate units represented by formula (L) are preferred. Examples thereof include bisphenol A/biphenol type copolymerized polycarbonate resins represented by formula (M) (wherein n/n+m is preferably 0.1 to 0.9, and more preferably 0.7 to 0.9).

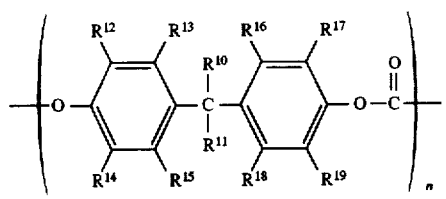

Polycarbonate wherein $R^{10}$ and $R^{11}$, which may combine cyclically, each independently represents a hydrogen atom, an alkyl group or an aryl group; $R^{12}$, $R^{13}$, $R^{14}$, $R^{15}$, $R^{16}$, $R^{17}$, $R^{18}$ and $R^{19}$ each independently represents a hydrogen atom, a halogen atom, an alkyl group or an aryl group; and n represents the molar number of the above-mentioned repeating units.

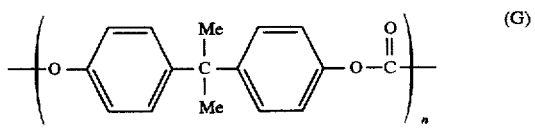

Bisphenol A Type Polycarbonate wherein n represents the molar number of the above-mentioned repeating units.

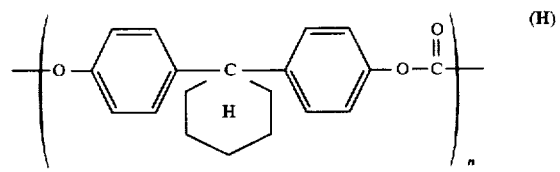

Bisphenol Z Type Polycarbonate wherein n represents the molar number of the above-mentioned repeating units.

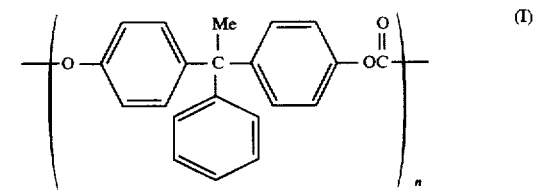

wherein n represents the molar number of the above-mentioned repeating units.

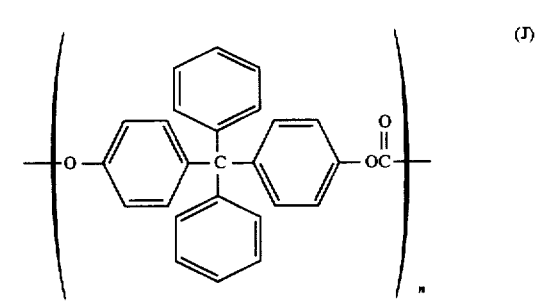

wherein n represents the molar number of the above-mentioned repeating units.

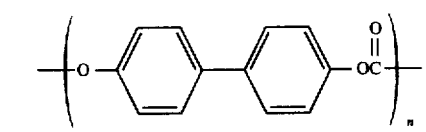

wherein n represents the molar number of the above-mentioned repeating units.

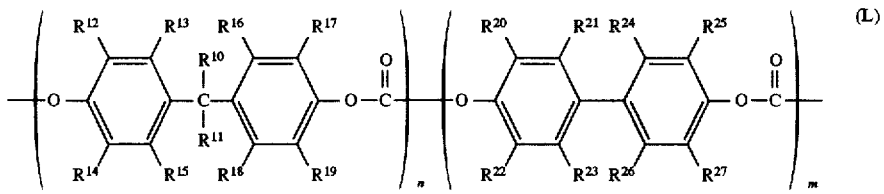

Bisphenol Copolymerized Polycarbonate wherein $R^{10}$ and $R^{11}$, which may combine cyclically, each independently represents a hydrogen atom, an alkyl group or an aryl group; $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ each independently represents a hydrogen atom, a halogen atom, an alkyl group or an aryl group; and m and n each represents the molar number of the above-mentioned repeating units.

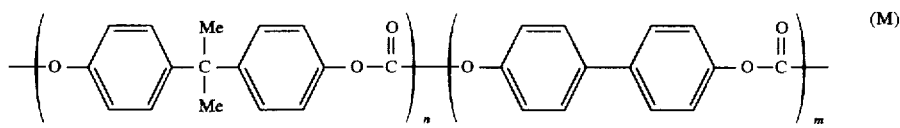

Bisphenol A/Biphenol Type Polycarbonate Resin wherein m and n each represents the molar number of the above-mentioned repeating units.

Further, besides the above-mentioned polycarbonates, a polycarbonate having repeating units represented by the following structural formula, which is disclosed in JP-A-6-214412, can be used.

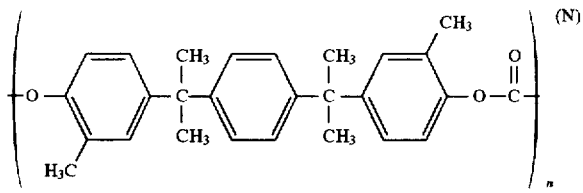

wherein n represents the molar number of the above-mentioned repeating units.

Furthermore, a polycarbonate represented by the following structural formula, which is disclosed in JP-A-6-222581, can also be used.

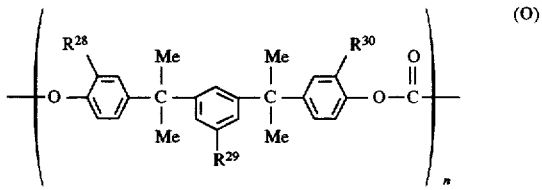

wherein $R^{28}$, $R^{29}$ and $R^{30}$, which may be the same or different, each represents a hydrogen atom, a halogen atom, an alkyl group, a cycloalkyl group, an aryl group or an arylalkyl group; and n represents the molar number of the above-mentioned repeating units.

For the mixing ratio of the binder to compound (1) of the present invention, the charge transporting material can be added in an amount of 10 to 1000 parts by weight, preferably 30 to 500 parts by weight, more preferably 40 to 200 parts by weight, per 100 parts by weight of binder.

There is no particular limitation on solvents used. Such solvents include alcohols such as methanol, ethanol and isopropanol, ketones such as acetone, methyl ethyl ketone and cyclohexanone, amides such as N,N-dimethylformamide and N,N-dimethylacetamide, sulfoxides such as dimethyl sulfoxide, ethers such as tetrahydrofuran, dioxane and ethylene glycol dimethyl ether, esters such as ethyl acetate and methyl acetate, aliphatic hydrocarbon halides such as methylene chloride, chloroform, 1,2-dichloroethane, dichloroethylene, trichloroethylene, trichloroethane and carbon tetrachloride, and aromatic compounds such as benzene, toluene, xylene chlorobenzene and dichlorobenzene. They may be used alone or as mixtures thereof.

The conductive supports used in the photoreceptors of the present invention include foils or plates of metals such as copper, aluminum, silver, iron, zinc and nickel or alloys thereof formed into the sheet form or the drum form, plastic films or cylinders over which these metals are vacuum deposited or electrolytically plated, or supports obtained by forming glass, paper or plastic films into the sheet form or the drum form, over which layers of conductive compounds such as conductive polymers, indium oxide and tin oxide are provided by coating or vapor deposition.

Coating can be conducted by use of coating methods such as dip coating, spray coating, spinner coating, wire bar coating, blade coating, roller coating and curtain coating.

Drying is preferably conducted by the method of heating at room temperature, followed by heat drying. It is preferred that the heat drying is generally performed at a temperature of 30° C. to 200° C. for 5 minutes to 2 hours in still or forced air.

Further, the charge transporting layers in the present invention can contain other charge transporting materials and various additives as required. Examples of the other charge materials include but are not limited to hydrazone compounds represented by the following general formula (I) described in JP-B-55-42380, JP-A-60-340999 and JP-A-61-23154, triphenylamine dimers represented by the following general formula (II) described in JP-B-58-32372, distyryl compounds represented by the following general formula (III) described in U.S. Pat. No. 3,873,312, tetraphenylbutadiene compounds, α-phenylstilbene, polyvinylcarbazole and triphenylmethane.

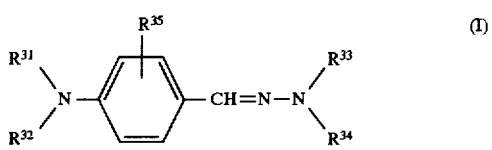

wherein $R^{31}$ and $R^{32}$, which may be the same or different, each represents a lower alkyl group, an aryl group which may have a substituent group, or an aralkyl group which may have a substituent group; $R^{33}$ and $R^{34}$, which may be the same or different, and which may combine to form a ring, each represents a lower alkyl group which may have a substituent group, an aryl group which may have a substituent group, an aralkyl group which may have a substituent group, or a heterocyclic group which may have a substituent group; and $R^{35}$, which may combine with $R^{31}$ or $R^{32}$ to form a ring, represents a hydrogen atom, a lower alkyl group, an aryl group which may have a substituent group, an aralkyl group which may have a substituent group, a lower alkoxy group or a halogen atom.

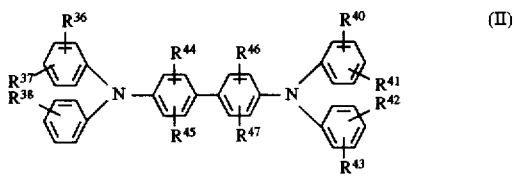

wherein $R^{36}$ to $R^{47}$, which may be the same or different, each represents a hydrogen atom, a lower alkyl group, a lower alkoxy group, a lower alkoxy group substituted by a halogen atom, an aryl group which may have a substituent group, or a halogen atom.

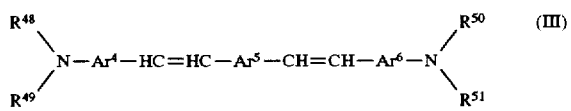

wherein $R^{48}$ to $R^{51}$, which may be the same or different, each represents a lower alkyl group or an aryl group which may have a substituent group; $Ar^4$ and $Ar^6$, which may be the same or different, each represents a phenyl group which may be substituted by at least one group selected from a lower alkyl group, a lower alkoxy group, an aryloxy group and a halogen atom; and $Ar^5$ represents a monocyclic or polycyclic aromatic ring having 4 to 14 carbon atoms which may have the same substituent group as with $Ar^4$ and $Ar^6$, or a heterocycle which may have the same substituent group as with $Ar^4$ and $Ar^6$.

The various additives include, for example, plasticizers such as biphenyl compounds disclosed in JP-A-6-332206, m-terphenyl and dibutyl phthalate, surface lubricants such as silicone oil, graft type silicone polymers and various fluorocarbons, potential stabilizers such as dicyanovinyl compounds and carbazole derivatives, monophenol antioxidants such as 2-tert-butyl-4-methylphenol and 2,6-di-tert-butyl-4-methylphenol, bisphenol antioxidants, amine antioxidants such as 4-diazabicyclo|2,2,2]octane, salicylic acid antioxidants and tocopherol.

The film thickness of the resulting charge transporting layer is 5 to 40 μm, and preferably 10 to 30 μm.

The charge transporting layer obtained as described above is electrically connected to the charge generating layer, thereby receiving the charge carrier injected from the charge generating layer in the presence of the electric field, and permitting the possession of the function of being able to transport the charge carrier to a surface of the photoreceptor. In this case, this charge transporting layer may be stacked on or under the charge generating layer. However, it is preferably stacked on the charge generating layer.

On the photosensitive layer thus prepared, a protective layer can be formed by coating as required. Materials for forming underlayers include polyvinyl alcohol, nitrocellulose, casein, ethylene-acrylic acid copolymers, polyamides such as nylon, polyurethane, gelatin and aluminum oxide. The film thickness of the underlayer is 0.1 to 5 μm, and preferably 0.5 to 3 μm.

With respect to the charge generating layers, materials selected from inorganic charge generating materials such as selenium, selenium-tellurium and amorphous silicon; cationic dyes such as pyrylium salt dyes, thiapyrylium salt dyes, azulenium salt dyes, thiacyanine dyes and quinocyanine dyes; polycyclic quinone pigments such as squarylium salt pigments, phthalocyanine pigments, anthanthrone pigments, dibenzpyrenequinone pigments and pyranthrone pigments; and organic charge generating materials such as indigo pigments, quinacridone pigments, azo pigments and pyrrolopyrrole pigments can be used alone or in combination as vapor deposited layers or coated layers.

Of the organic charge generating materials as described above, organic charge generating materials described in Chem. Rev., 93, 449–486 (1993) are particularly preferred.

In particular, the phthalocyanine pigments include alkoxytitanium phthalocyanine (Ti(OR)$_2$Pc), oxotitanium phthalocyanine (TiOPc), copper phthalocyanine (CuPc), metal-free phthalocyanine (H$_2$Pc), hydroxygallium phthalocyanine (HOGaPc), vanadyl phthalocyanine (VOPc) and chloroindium phthalocyanine (ClInPc). More particularly, TiOPc includes α-TiOPc, β-TiOPc, γ-TiOPc, m-TiOPc, Y-TiOPc, A-TiOPc, B-TiOPc and amorphous TiOPc. H$_2$Pc includes α-H$_2$Pc, β-H$_2$Pc, τ-H$_2$Pc and X-H$_2$Pc.

These phthalocyanines can be used as mixtures obtained by mixing and milling, or as newly formed mixed crystal systems. For example, mixed crystals of oxotitanyl phthalocyanine and vanadyl phthalocyanine described in JP-A-4-371962, JP-A-5-2278 and JP-A-5-2279, and mixed crystals of oxotitanyl phthalocyanine and chloroindium phthalocyanine described in JP-A-6-148917, JP-A-6-145550, JP-A-6-271786 and JP-A-5-297617 can be used.

Further, as the azo compounds, compounds represented by the following structural formulas are preferred.

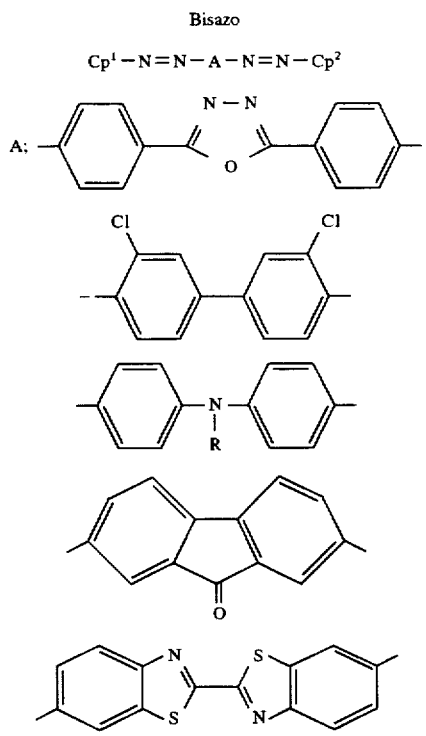

wherein R represents a lower alkyl group.

Trisazo

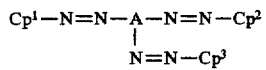

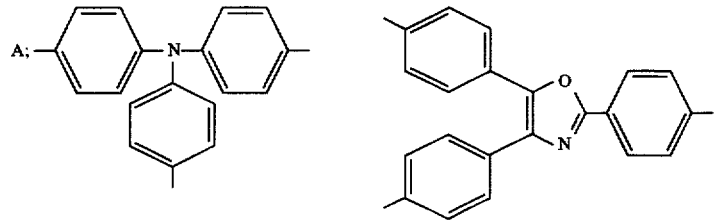

Cp¹ and Cp² of bisazo, and Cp¹, Cp² and Cp³ of trisazo

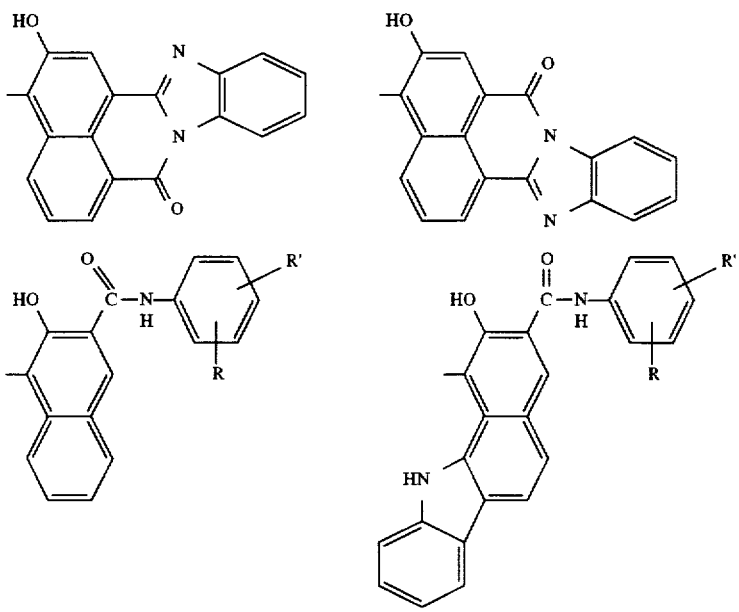

wherein R and R', which may be the same or different, each represents a hydrogen atom, a halogen group or a lower alkyl group.

wherein R and R', which may be the same or different, each represents a hydrogen atom, a halogen group or a lower alkyl group.

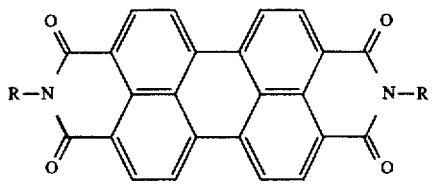

wherein R represents a hydrogen atom, a lower alkyl group or an aryl group.

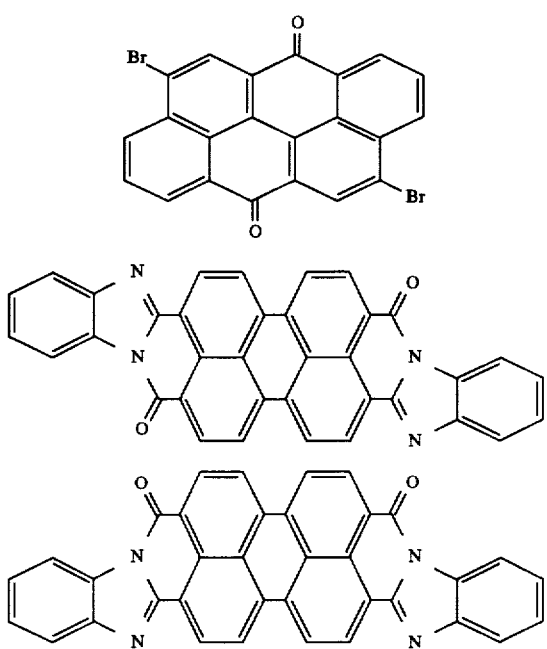

In addition to these, any materials can be used as long as they are materials absorbing light and generating charge at high efficiency.

As described above, the electrophotographic photoreceptors containing carbazole derivatives (1) of the compounds of the present invention in the charge transporting layers can be obtained.

As described above, carbazole derivatives (1) of the compounds of the present invention, namely the compounds as mentioned in Tables 1 and 2, are materials which are stable when formed into films, can exhibit high carrier mobility, and are also excellent in various characteristics when they form electrophotographic photoreceptors.

EXAMPLES

The present invention will be described with reference to examples below, but these are not to be construed as limiting the invention. Measuring instruments and measuring conditions used in the examples are shown below:

(1) $^1$H-NMR

Instrument: Type AM-400 (400 MHz) manufactured by Bruker, Inc.

Solvent: $CDCl_3$ or $C_6D_6$

Internal Standard Material: Tetramethylsilane (2) MASS

Instrument: Hitachi M-80 B (manufactured by Hitachi, Ltd.)

EXAMPLE 1

Synthesis of 3,6-Bis(2',2'-diphenylvinyl)-9-ethyl-carbazole (Exemplified Compound 4, m=n=0, $Ar^1=R^1=Ar^2=R^2=Ph$, $R^3$=an ethyl group)

(1) 3,6-Diformyl-9-ethylcarbazole (2a)

138.8 g (1.02 mol) of zinc chloride was weighed and put in a 2-liter reaction flask, and 1 liter of toluene was added, followed by dehydration under reflux for 3 hours. The solution was cooled to room temperature, and 100 g (0.51 mol) of ethylcarbazole (4a) (manufactured by Tokyo Kasei Kogyo Co.) and 267.9 g (3.67 mol) of N,N-dimethylformamide were added. Subsequently, 468.3 g (3.05 mol) of phosphorus oxychloride was added elevating the temperature from room temperature to 80° C. over a period of 30 minutes. The flask was heated to 82° C. in an oil bath and stirred for 72 hours. After cooling, the mixture was poured into 5 liters of ice water, and sodium carbonate was slowly added to make the solution basic (pH 10–11). Then, 1 liter of toluene was added, and the resulting solution was stirred at 60° C. for 1 hour. After standing, solution separation was carried out. The toluene phase was washed with water (3 liters×3), dried ($MgSO_4$), and concentrated. The resulting crude crystals (132.1 g) were recrystallized twice from toluene, thus obtaining 79.23 g of 3,6-diformyl-9-ethylcarbazole (2a).

Yield; 62.9%, m.p.; 117°–178.5° C.

MS; 251($M^+$), 236, 222, 207, 193, 178, 166, 152

$^1$H-NMR (δ; ppm in $CDCl_3$); 1.50 (t, J=7.3 Hz, 3H), 4.45 (q, J=7.3 Hz, 2H), 7.55 (d, J=8.5 Hz, 2H), 8.09 (dd, J=8.5 Hz, J=1.6 Hz, 2H), 8.65 (s, 2H), 10.12 (s, 2H)

(2) 3,6-Bis(2',2'-diphenylvinyl)-9-ethylcarbazole (Exemplified Compound 4)

In 20 ml of N,N-dimethylformamide, 2 g (7.9 mmol) of 3,6-diformyl-9-ethylcarbazole (2a) and 5.63 g (175 mmol) of diethyl diphenylmethylphosphite were dissolved, and 2.14 g (19.1 mmol) of potassium-t-butoxide was slowly added. Reaction was conducted at 50° C. for 17 hours, and the reaction product was poured into 300 ml of water. After extraction with 200 ml of benzene, the organic layer was washed with water (300 ml×3), dried ($MgSO_4$), and concentrated. The residue was applied to silica gel column chromatography (eluent; toluene) to obtain 3.94 g of crystals. The crystals were recrystallized from a mixed solvent of toluene and heptane (1/1 by weight), thus obtaining 3.41 g of exemplified compound 4.

Yield; 77.8%, m.p.; 178.5°–179.5° C.

MS; 551, 523, 275, 178

$^1$H-NMR (δ; ppm in $CDCl_3$); 1.32 (t, J=7.2 Hz, 3H), 4.18 (q, J=7.2 Hz, 2H), 7.07 (m, 4H), 7.13 (s, 2H), 7.23–7.39 (m, 16H), 7.52 (s, 2H)

EXAMPLE 2

Synthesis of 3-(2',2'-diphenylvinyl)-6-(2",2"-di-m-tolylvinyl)-9-ethylcarbazole (Exemplified Compound 5, m=n=0, $Ar^1=R^1=Ph$, $Ar^2=R^2=Ph$-(3)Me, $R^3$=an ethyl group)

(1) 3-(2',2'-Diphenylvinyl)-9-ethylcarbazole (6a)

25.3 g (111.7 mmol) of 3-formyl-9-ethylcarbazole (2') (manufactured by Tokyo Kasei Kogyo Co.), 39.6 g (122.9 mmol) of diethyl diphenylmethylphosphite, 253 ml of DMF and 15.04 g (134.0 mmol) of potassium-t-butoxide were allowed to react and after treated in the same manner as with Example 1 (2) to obtain 36.44 g of 3-(2',2'-diphenylvinyl)-9-ethylcarbazole.

Yield; 86.7%, m.p.; 145°–146° C.

MS; 374, 358, 280, 178

$^1$H-NMR (δ; ppm in $CDCl_3$); 1.38 (t, J=7.2 Hz, 3H), 4.28 (q, J=7.2 Hz, 2H), 7.12–7.20 (m, 4H), 7.24–7.44 (m, 12H), 7.72 (s, 1H), 7.81 (d, J=7.7 Hz, 1H)

(2) 3-(2',2'-Diphenylvinyl)-6-formyl-9-ethylcarbazole (5a)

35.4 g (87.87 mmol) of 3-(2',2'-diphenylvinyl)-9-ethylcarbazole (6a), 46.2 g (631.8 mmol) of DMF, 23.9 g (175.5 mmol) of zinc chloride, 80.7 g (526.6 mmol) of phosphorus oxychloride and 354 g of toluene were allowed to react and after treated in the same manner as with Example 1 (1). The crude product was treated by silica gel column chromatography (eluent; benzene/ethyl acetate=9/1 by volume), and recrystallized from a mixed solvent of toluene and heptane (3/2 by weight), thus obtaining 10.5 g of 3-(2',2'-diphenylvinyl)-6-formyl-9-ethylcarbazole.

Yield; 25.5%, m.p.; 166°–167° C.

MS; 401(M⁺), 386

¹H-NMR (δ; ppm in CDCl₃); 1.40 (t, J=7.2 Hz, 3H), 4.30 (q, J=7.2 Hz, 2H), 7.19 (m, 3H), 7.22–7.43 (m, 11H), 7.79 (s, 1H), 7.97 (dd, J=8.6 Hz, J=1.6 Hz, 1H), 8.33 (s, 1H), 10.02 (s, 1H)

(3) Synthesis of 3-(2',2'-diphenylvinyl)-6-(2",2"-di-m-tolylvinyl)-9-ethylcarbazole (exemplified compound 5)

2.0 g (4.76 mmol) of 3-(2',2'-diphenylvinyl)-6-formyl-9-ethylcarbazole (5a), 1.88 g (5.23 mmol) of diethyl di-m-tolylmethylphosphite, 20 ml of DMF and 0.64 g (5.70 mmol) of potassium-t-butoxide were allowed to react and after treated in the same manner as with Example 1 (2) to obtain 2.2 g of exemplified compound 5.

Yield; 79.0%, m.p.; 166°–167° C.

MS; 579, 401, 91

¹H-NMR (δ; ppm in CDCl₃); 1.34 (t, J=7.1 Hz, 3H), 2.30 (s, 3H), 2.36 (s, 3H), 4.19 (q, J=7.2 Hz, 2H), 7.02–7.11 (m, 8H), 7.12–7.17 (m, 3H), 7.18–7.30 (m, 6H), 7.30–7.40 (m, 7H), 7.57 (d, J=3.8 Hz, 2H)

EXAMPLE 3

Synthesis of 3-(2',2'-Diphenylvinyl)-6-(4",4"-diphenylbutadienyl)-9-ethylcarbazole (Exemplified Compound 6, m=0, n=1, Ar¹=R¹=Ar²=R²=Ph, R³=an ethyl group)

(1) Synthesis of 1,1-Diphenylethylene (9a)

A 2-liter reaction flask was charged with 31.6 g (1.3 mol) of magnesium and 50 ml of dry THF in a stream of nitrogen, and iodine and ethyl bromide were added in trace amounts to confirm the initiation of reaction. Then, 600 ml of dry THF was added with stirring, and methyl chloride gas was blown in. The amount of the blown-in gas and cooling were controlled so as to keep 30°–40° C. When 2 hours elapsed, heat development ceased, and magnesium disappeared. The blowing-in of the methyl chloride gas was stopped, followed by stirring at the same temperature for 1 hour, thus completing the preparation of a Grignard reagent.

Then, a mixed solution of 182.22 g (1.1 mol) of benzophenone (8a, Ar=R=Ph) and 364 ml of THF was added dropwise at 35° to 40° C. for 30 minutes, followed by stirring at the same temperature for 2 hours and further stirring at the same temperature for 13 hours, thus terminating the reaction. The reaction product was poured into 1400 g of a cooled 10% aqueous solution of ammonium chloride, followed by stirring for 30 minutes. After standing and solution separation, the resulting product was washed with brine, dried over magnesium sulfate, and concentrated to obtain 200.23 g (the theoretical yield from benzophenone is 98.6%) of crude carbinol.

200.23 g of crude carbinol, 400 ml of toluene and 1 g of paratoluenesulfonic acid (PTSA) were weighed and put in a 1-liter reaction flask, and azeotropic dehydration was carried out under toluene refluxing (94°–116° C.) for 2 hours. The resulting product was washed with water after cooling, washed with a 2% aqueous solution of soda ash, washed with water, dried over magnesium sulfate, and concentrated to obtain 190.09 g of crude 1,1-diphenylethylene (9a, Ar=R=Ph). Crude 1,1-diphenylethylene (9a) was distilled in a Claisen flask equipped with a vigreux to obtain 174.06 g of 1,1-diphenyl-ethylene (9a).

B.p.; 103° C./1 mm Hg

The yield from benzophenone was 96.5%.

(2) Synthesis of 3,3-Diphenylallyl Chloride (10a, Ar=R=Ph)

A 300-ml reaction flask was charged with 54.13 g (0.3 mol) of 1,1-diphenylethylene (9a), 108.26 g of acetic acid and 13.51 g (0.45 mol) of paraformaldehyde, and 13.67 g (0.375 mol) of hydrogen chloride was blown in with stirring at 30° C. for 3.5 hours. The reaction temperature was kept at 30° C. by cooling because of weak heat development. The blowing-in of hydrogen chloride was stopped, and the solution was stirred at the same temperature for 2 hours, followed by standing overnight. The reaction solution was poured into 200 ml of water, followed by extraction with 200 ml of toluene. The resulting product was washed with water, washed with 2% soda ash, washed with water, dried over magnesium sulfate, and concentrated to obtain 68.42 g of a crude chloride. It was distilled in a Claisen flask equipped with a vigreux to obtain 57.51 g.

B.p.; 120°–132° C./1 mm Hg

Yield; 79%

MS; 228(M⁺), 193, 178, 115

¹H-NMR (δ; ppm in CDCl₃); 4.11 (2H, d, J=8.0 Hz), 6.23 (1H, t, J=8.0 Hz), 7.21–7.41 (10H, m)

(3) Synthesis of Diethyl 3,3-Diphenylallylphosphite (7a, Ar=R=Ph)

40.75 g (0.155 mol) of 3,3-diphenylallyl chloride (10a) and 94.48 g (0.569 mol) of triethyl phosphite were stirred under reflux for 24 hours. The confirmation of disappearance of 3,3-diphenylallyl chloride (10a) was taken as termination of the reaction. After cooling, the reaction product was distilled in a Claisen flask equipped with a vigreux to obtain 55.39 g.

B.p.; 170°–203° C./1 mm Hg

Theoretical yield; 99%

MS; 330 (M⁺), 193, 115

¹H-NMR (δ; ppm in CDCl₃); 1.31 (6H, t, J=7.0 Hz), 2.71 (2H, dd, J=7.9 Hz, J=22.4 Hz), 4.08 (6H, dt, J=7.1 Hz, J=7.6 Hz), 6.12 (1H, q, J=7.9 Hz, J=7.6 Hz), 7.22–7.38 (10H, m)

(4) 3-(2',2'-Diphenylvinyl)-6-(4",4"-diphenylbutadienyl)-9-ethylcarbazole (Exemplified Compound 6)

2.0 g (4.76 mmol) of 3-(2',2'-diphenylvinyl)-6-formyl-9-ethylcarbazole (5a), 1.73 g (5.24 mmol) of diethyl 3,3-diphenylallylphosphite, 40 ml of DMF and 0.64 g (5.70 mmol) of potassium-t-butoxide were allowed to react and after treated in the same manner as with Example 1 (2) to obtain 2.02 g of exemplified compound 6.

Yield; 72.1%, m.p.; 122°–123° C.

MS; 577, 368, 91

¹H-NMR (δ; ppm in CDCl₃); 1.36 (t, J=7.2 Hz, 3H), 4.23 (q, J=7.3 Hz, 2H), 6.87–6.97 (m, 3H), 7.09–7.50 (m, 25H), 7.60 (s, 1H), 7.72 (d, J=1.5 Hz, 1H)

EXAMPLE 4

Synthesis of 3,6-Bis(4',4'-diphenylbutadienyl)-9-ethylcarbazole (Exemplified Compound 12, m=n=1, Ar¹=R¹=Ar²=R²=Ph, R³=an ethyl group)

2.0 g (7.95 mmol) of 3,6-diformyl-9-ethylcarbazole (2a), 5.78 g (17.5 mmol) of diethyl 3,3-diphenylallylphosphite, 20 ml of DMF and 2.14 g (19.07 mmol) of potassium-t-butoxide were allowed to react and after treated in the same manner as with Example 1 (2) to obtain 4.61 g of exemplified compound 12.

Yield; 95.3%, m.p.; 163.5°–164.5° C.

MS; 603(M⁺), 412

¹H-NMR (δ; ppm in CDCl₃); 1.38 (t, J=7.0 Hz, 3H), 4.28 (q, J=7.0 Hz, 2H), 6.93 (s, 6H), 7.12–7.19 (m, 6H), 7.22–7.37 (m, 9H), 7.38–7.520 (m, 9H), 7.97 (d, J=1.4 Hz, 2H)

EXAMPLE 5

Synthesis of 3,6-Bis(2',2'-diphenylvinyl)-9-isopropylcarbazole (Exemplified Compound 14, m=n=0, $Ar^1=R^1=Ar^2=R^2=Ph$, $R^3$=an isopropyl group)

(1) 9-Isopropylcarbazole (4b)

16 g (95.7 mmol) of carbazole, 38 g (608.2 mmol) of 85% KOH, 21 g (151.9 mmol) of potassium carbonate, 3.2 g (9.4 mmol) of tetra-n-butylammonium hydrogensulfate and 300 ml of toluene were weighed and put in a 1-liter four neck flask, and 25 g (147.1 mmol) of 2-iodopropane was added little by little from a dropping funnel (heat is slightly developed). Subsequently, the reaction was conducted at a temperature of 60° C. to 80° C. for 7 hours. The disappearance of carbazole was confirmed by TLC and gas chromatography. After cooling, the solution was filtered, and the filtrate was washed with water three times. The toluene phase was dried (MgSO$_4$), and concentrated, thus obtaining 21.5 g of a crude product. The crude product was recrystallized from 2-propanol to obtain 16.35 g of a desired product.

Yield; 81.6%, m.p.; 124°–125° C.

MS; 209, 194, 167, 138

$^1$H-NMR (δ; ppm in CDCl$_3$); 1.71 (d, J=7.0 Hz, 6H), 5.00 (sextet, 1H), 7.21 (t, J=7.0 Hz, 2H), 7.43 (t, J=7.1 Hz, 2H), 7.53 (d, J=8.3 Hz, 2H), 8.11 (d, J=7.8 Hz, 2H)

(2) 3,6-Diformyl-9-isopropylcarbazole (2b)

10.0 g (47.8 mmol) of 9-isopropylcarbazole (4b), 14.2 g (194.3 mmol) of DMF, 7.0 g (51.4 mmol) of zinc chloride, 30.0 g (195.7 mmol) of phosphorus oxychloride and 100 ml of toluene were allowed to react and after treated in the same manner as with Example 1 (1) to obtain 7.78g of 3,6-diformyl-9-isopropylcarbazole (2b).

Yield; 61.3%, m.p.; 143°–144° C.

MS; 313(M$^+$), 91

$^1$H-NMR (δ; ppm in CDCl$_3$); 5.60 (s, 2H), 7.13 (m, 2H), 7.25–7.35 (m, 3H), 7.53 (d, J=8.6 Hz, 2H), 8.05 (d, J=8.6 Hz, 2H), 8.72 (s, 2H), 10.15 (s, 2H)

(3) 3,6-Bis(2',2'-diphenylvinyl)-9-isopropylcarbazole (Exemplified Compound 14)

2.0 g (7.95 mmol) of 3,6-diformyl-9-isopropylcarbazole (2b), 5.54 g (18.24 mmol) of diethyl diphenylmethylphosphite, 20 ml of DMF and 2.20 g (19.61 mmol) of potassium-t-butoxide were allowed to react and after treated in the same manner as with Example 1 (2) to obtain 2.98 g of exemplified compound 14

Yield; 70.0%, m.p.; 130°–133° C.

MS; 566, 522, 304, 283, 202, 179

$^1$H-NMR (δ; ppm in CDCl$_3$); 1.60 (d, J=7.0 Hz, 6H), 4.78 (sextet, J=7.0 Hz, 1H), 7.04 (dd, J=9.0 Hz, J=1.8 Hz, 2H), 7.12 (s, 2H), 7.17 (d, J=8.7 Hz, 2H), 7.22–7.40 (m, 20H), 7.52 (s, 2H)

EXAMPLE 6

Synthesis of 3,6-Bis(4',4'-diphenylbutadienyl)-9-isopropylcarbazole (Exemplified Compound 15, m=n=1, $Ar^1=R^1=Ar^2=R^2=Ph$, $R^3$=an isopropyl group)

2.0 g (7.54 mmol) of 3,6-diformyl-9-isopropylcarbazole (2b), 5.50 g (16.65 mmol) of diethyl 3,3-diphenylallylphosphite, 20 ml of DMF and 2.0 g (17.82 mmol) of potassium-t-butoxide were allowed to react and after treated in the same manner as with Example 1 (2) to obtain 3.02 g of exemplified compound 15.

Yield; 64.8%, m.p.; 154°–157° C.

MS; 617(M$^+$), 426, 382, 309

$^1$H-NMR (δ; ppm in CDCl$_3$); 1.65 (d, J=7.0 Hz, 6H), 4.88 (sextet, J=7.0 Hz, 1H), 6.90–6.95 (m, 6H), 7.21–7.49 (m, 24H), 7.99 (s, 2H)

EXAMPLE 7

Synthesis of 3,6-Bis(4'-phenyl-4'-p-tolylbutadienyl)-9-isopropylcarbazole (Exemplified Compound 16, m=n=1, $Ar^1=Ar^2=Ph$, $R^1=R^2=Ph$-(4)Me, $R^3$=an isopropyl group)

(1) Synthesis of 1-Phenyl-1'-(p-tolyl)ethylene (9b, Ar=Ph, R=Ph-(4)Me)

A Grignard solution was prepared from 3.7 g (152.2 mmol) of magnesium, 70 ml of THF and methyl chloride gas in the same manner as with Example 3 (1), and allowed to react with a solution of 25 g (127.1 mmol) of 4-methylbenzophenone in 40 ml of THF. Hereinafter, the reaction product was after treated and dehydrated with paratoluenesulfonic acid in the same manner as with Example 3 (1) to obtain 19.5 g of 1-phenyl-1'-(p-tolyl)ethylene (9b).

Yield; 79.0%, b.p.; 90°–95° C./1 mm Hg

MS (GC); 194, 179, 165, 115, 89, 63, 51

(2) Synthesis of 3-Phenyl-3-(p-tolyl)allyl Chloride (10b, Ar=Ph, R=Ph-(4)Me)

8.77 g (44.9 mmol) of 1-phenyl-1'-(p-tolyl)ethylene (9b), 2.02 g (67.3 mmol) of paraformaldehyde and hydrogen chloride gas were allowed to react, and after treated in the same manner as with Example 3 (2) to obtain 7.65 g of 3-phenyl-3-(p-tolyl)allyl chloride (10b).

Yield; 70.2%, b.p.; 149°–180° C./1 mm Hg (3) Synthesis of Diethyl 3-Phenyl-3-(p-tolyl)allyl phosphite (7b, Ar=Ph, R=Ph-(4)Me)

7.65 g (31.5 mmol) of 3-phenyl-3-(p-tolyl)allyl chloride (10b) was allowed to react with 26.18 g (157.6 mmol) of triethyl phosphite in the same manner as with the synthesis of diethyl 3,3-diphenylallylphosphite (7a) in Example 3 (3), followed by distillation under reduced pressure to obtain 10.12 g of diethyl 3-phenyl-3-(p-tolyl)allylphosphite (7b) as an oily product.

Theoretical yield; 93.3%

B.p.; 213°–260° C./1 mm Hg

MS (GC); 344,207, 165, 115, 91

$^1$H-NMR (δ; ppm in CDCl$_3$); 1.31 (6H, t, J=7.1 Hz), 2.30, 2.38 (3H, s), 2.62–2.78 (2H, m), 4.07 (4H, m), 6.08 (1H, q, J=7.3 Hz), 7.06–7.40 (9H, m)

(4) 3,6-Bis(4'-phenyl-4'-p-tolylbutadienyl)-9-isopropylcarbazole (Exemplified Compound 16)

2.0 g (7.54 mmol) of 3,6-diformyl-9-isopropylcarbazole (2b), 5.70 g (16.55 mmol) of diethyl 3-phenyl-3-p-tolylallylphosphite, 20 ml of DMF and 2.0 g (17.82 mmol) of potassium-t-butoxide were allowed to react and after treated in the same manner as with Example 1 (2) to obtain 3.33 g of exemplified compound 16.

Yield; 68.4%, m.p.; 138°–141° C.

MS; 645(M$^+$), 181

$^1$H-NMR (δ; ppm in CDCl$_3$); 1.65 (m, 6H), 2.37, 2.46 (s, 6H), 4.89 (m, 1H), 6.87–6.97 (m, 6H), 7.12 (d, J=7.9 Hz, 2H), 7.20–7.48 (m, 20H), 7.97 (m, 2H)

EXAMPLE 8

Synthesis of 3,6-Bis(4',4'-diphenylbutadienyl)-9-phenylcarbazole (Exemplified Compound 21, m=n=1, $Ar^1=R^1=Ar^2=R^2=Ph$, $R^3$=a phenyl group)

(1) 3,6-Diformyl-9-phenylcarbazole (2c)

23.0 g (93.1 mmol) of 9-phenylcarbazole (4c) (manufactured by Aldrich Co.), 49.0 g (670.5 mmol) of DMF, 25.4 g (186.2 mmol) of zinc chloride, 85.7 g (558.7 mmol) of phosphorus oxychloride and 230 ml of toluene were allowed to react and after treated in the same manner as with Example 1 (1) to obtain 11.8 g of 3,6-diformyl-9-phenylcarbazole (2c).

Yield; 42.2%, m.p.; 193°–194° C.

MS; 299(M⁺), 270, 241, 84

¹H-NMR (δ; ppm in CDCl₃); 7.46 (d, J=8.5 Hz, 2H), 7.53–7.62 (m, 3H), 7.66–7.71 (m, 2H), 8.02 (dd, J=8.6 Hz, J=1.6 Hz, 2H), 8.72 (s, 2H), 10.15 (s, 2H)

(2) 3,6-Bis(4',4'-diphenylbutadienyl)-9-phenylcarbazole (Exemplified Compound 21)

2.0 g (6.66 mmol) of 3,6-diformyl-9-phenylcarbazole (2c), 4.84 g (14.65 mmol) of diethyl 3,3-diphenylallylphosphite, 20 ml of DMF and 1.79 g (15.95 mmol) of potassium-t-butoxide were allowed to react and after treated in the same manner as with Example 1 (2) to obtain 3.81 g of exemplified compound 21.

Yield; 87.8%, m.p.; 130°–131° C.

MS; 651(M⁺), 440

¹H-NMR (δ; ppm in CDCl₃); 6.94 (s, 2H), 7.12–7.60 (m, 29H), 8.01 (s, 2H)

EXAMPLE 9

Synthesis of 3,6-Bis(2',2'-diphenylvinyl)-9-p-tolylcarbazole (Exemplified Compound 22, m=n=0, Ar¹=R¹=Ar²=R²=Ph, R³=a p-tolyl group)

(1) 9-p-Tolylcarbazole (4d)

10.0 g (59.8 mmol) of carbazole, 17.0 g (78.0 mmol) of 4-iodotoluene, 11.0 g (79.6 mmol) of potassium carbonate and 760 mg (12.0 mmol) of copper powder were allowed to react in 200 ml of diisopropylbenzene at 210° C. for 30 hours. The mixture was cooled to 80°–90° C., and filtered on sellaite. The filtrate was concentrated, and the residue was recrystallized from isopropanol to obtain 11.8 g of 9-p-tolylcarbazole.

Yield; 76.7%, m.p.; 113°–114° C.

MS; 257(M⁺), 241, 228, 166, 140, 128, 91, 65

¹H-NMR (δ; ppm in CDCl₃); 2.45 (s, 3H), 7.23–7.28 (m, 2H), 7.35–7.45 (m, 8H), 8.12 (d, J=7.8 Hz, 2H)

(2) 3,6-Diformyl-9-p-tolylcarbazole (2d)

50.0 g (0.19 mol) of 9-p-tolylcarbazole (4c), 100.0 g (1.37 mol) of DMF, 51.8 g (0.38 mol) of zinc chloride, 174.8 g (1.14 mol) of phosphorus oxychloride and 500 g of toluene were allowed to react and after treated in the same manner as with Example 1 (1), and treated by silica gel column chromatography (eluent: toluene/ethyl acetate=9/1 by volume) to obtain 16.65 g of crude crystals. These crystals were recrystallized from toluene to obtain 14.33 g of 3,6-diformyl-9-p-tolylcarbazole.

Yield; 23.9%, m.p.; 229°–230° C.

MS; 313(M⁺), 284, 269, 255, 241, 84

¹H-NMR (δ; ppm in CDCl₃); 2.52 (s, 3H), 7.39–7.48 (m, 6H), 8.01 (dd, J=1.6 Hz, 2H), 8.72 (s, 2H), 10.12 (s, 2H) (3) 3,6-Bis(2',2'-diphenylvinyl)-9-p-tolylcarbazole (Exemplified Compound 22)

2.0 g (6.35 mmol) of 3,6-diformyl-9-p-tolylcarbazole (2c), 4.5 g (13.96 mmol) of diethyl diphenylmethylphosphite, 60 ml of DMF and 1.71 g (15.24 mmol) of potassium-t-butoxide were allowed to react and after treated in the same manner as with Example 1 (2) to obtain 3.01 g of exemplified compound 22.

Yield; 77.1%, m.p.; 205°–206° C.

MS; 613(M⁺), 306,179, 43

¹H-NMR (δ; ppm in CDCl₃); 2.42 (s, 3H), 7.00 (dd, J=8.8 Hz, J=1.6 Hz, 2H), 7.05 (d, J=8.6 Hz, 2H), 7.14 (s, 2H), 7.23–7.40 (m, 24H), 7.57 (s, 2H)

EXAMPLE 10

Synthesis of 3,6-Bis(4',4'-diphenylbutadienyl)-9-p-tolylcarbazole (Exemplified Compound 23, m=n=1, Ar¹=R¹=Ar²=R²=Ph, R³=a p-tolyl group)

2.0 g (6.35 mmol) of 3,6-diformyl-9-p-tolylcarbazole (2d), 4.62 g (13.98 mmol) of diethyl 3,3-diphenylallylphosphite, 120 ml of DMF and 1.71 g (15.24 mmol) of potassium-t-butoxide were allowed to react and after treated in the same manner as with Example 1 (2) to obtain 2.52 g of exemplified compound 23.

Yield; 59.0%, m.p.; 251.5°–252.5° C.

MS; 665(M⁺), 474, 396, 337, 205, 167, 57

¹H-NMR (δ; ppm in CDCl₃); 2.48 (s, 3H), 6.93 (s, 6H), 7.20–7.48 (m, 28H), 8.00 (s, 2H)

EXAMPLE 11

Synthesis of 3,6-Bis(4',4'-di-p-tolylbutadienyl)-9-benzylcarbazole (Exemplified Compound 25,-m=n=1, Ar¹=Ar²=R¹=R²=Ph-(4)Me, R³=a benzyl group)

(1) 9-Benzylcarbazole (4e)

20 g (119.6 mmol) of carbazole, 47 g (712.0 mmol) of 85% KOH, 26.5 g (191.7 mmol) of potassium carbonate, 4.0 g (11.8 mmol) of tetra-n-butylammonium hydrogensulfate, 17.0 g (134.3 mmol) of benzyl chloride and 300 ml of toluene were allowed to react and after treated in the same manner as with Example 7 (1) to obtain 26.88 g of 9-benzylcarbazole.

Yield; 87.3%, m.p.; 121°–122° C.

MS; 257(M⁺), 180, 166, 91

¹H-NMR (δ; ppm in CDCl₃); 5.50 (s, 2H), 7.12 (m, 2H), 7.17–7.27 (m, 5H), 7.34 (d, J=8.2 Hz, 2H), 7.42 (m, 2H), 8.10 (d, J=6.7 Hz, 2H)

(2) 3,6-Diformyl-9-benzylcarbazole (2e)

7.0 g (27.2 mmol) of 9-benzylcarbazole (4d), 11.8 g (161.4 mmol) of DMF, 4.0 g (29.3 mmol) of zinc chloride, 17.0 g (110.9 mmol) of phosphorus oxychloride and 100 ml of toluene were allowed to react and after treated in the same manner as with Example 1 (1), and treated by silica gel column chromatography (eluent: toluene, and then ethyl acetate) to obtain crystals. These crystals were recrystallized from ethyl acetate toluene to obtain 3.0 g of 3,6-diformyl-9-benzylcarbazole.

Yield; 23.5%, m.p.; 222°–224° C.

MS; 313(M⁺), 91

¹H-NMR; 5.60 (s, 2H), 7.13 (m, 2H), 7.25–7.35 (m, 3H), 7.53 (d, J=8.6 Hz, 2H), 8.05 (d, J=8.6 Hz, 2H), 8.72 (s, 2H), 10.15 (s, 2H)

(3) Synthesis of 1,1-Di(p-tolyl)ethylene (9c, Ar=R=Ph-(4)Me)

15.6 g (0.65 mol) of magnesium and 20 ml of THF were placed in a 1-liter reaction flask in a stream of nitrogen, the reaction was initiated with a small amount of ethyl iodide and iodine, and a solution of 111.15 g (0.65 mol) of p-bromotoluene in 500 ml of THF was added dropwise at a temperature from room temperature to 40° C. for 2 hours to prepare a Grignard reagent. A solution of 83.75 g (0.625 mol) of p-methylacetophenone (11c) in 200 ml of THF was added dropwise thereto at the same temperature for 3 hours. The resulting solution was stirred at room temperature for 3 hours, and subsequently stirred under reflux for 4 hours. Then, the solution was cooled, and poured into 1 liter of 5% aqueous sulfuric acid to conduct hydrolysis. The resulting product was extracted with toluene, and the extract was washed with aqueous soda ash, washed with water, and concentrated. Then, 300 ml of toluene and 0.5 g of PTSA were added thereto, followed by stirring under reflux for 4 hours to carry out azeotropic dehydration. The resulting product was washed with aqueous soda ash, washed with water, and concentrated. Crude 1,1-di(p-tolyl)ethylene (9c) was distilled in a Claisen flask equipped with a vigreux to obtain 98.5 g.

B.p.; 120°–121° C./1 mm Hg

The yield from p-methylacetophenone is 75.8%.

(4) Synthesis of 3,3-Di(p-tolyl)allyl Chloride (10c, Ar=R=Ph-(4)Me

In the same manner as with the synthesis of 3,3-diphenylallyl chloride (10a) in Example 3 (2), 58.7 g of 3,3-di(p-tolyl)allyl chloride (10c) (b.p.; 153°–173° C./1 mm Hg, yield; 67.9%) was obtained from 70.5 g 0.337 mol) of 1,1-di(p-tolyl)ethylene (9c), 15.1 g (0.505 mol) of paraformaldehyde and hydrogen chloride gas. This was recrystallized from hexane to obtain 49.0 g.

M.p.; 66° C.
Theoretical yield; 56.7%
MS; 256(M$^+$), 221,206, 165, 129
$^1$H-NMR (δ; ppm in CDCl$_3$); 2.33 (3H, s), 2.39 (3H, s), 4.13 (2H, d, J=8.1 Hz), 6.17 (1H, t, J=8.1 Hz), 7.01–7.24 (8H, m)

(5) Synthesis of Diethyl 3,3-Di(p-tolyl)allylphosphite (7c, Ar=R=Ph-(4)Me)

In the same manner as with the synthesis of diethyl 3,3-Diphenylallylphosphite (7a) in Example 3 (3), 35.0 g (0.1365 mol) of 3,3-di(p-tolyl)allyl chloride (10c) was allowed to react with 68 g (0.409 mol) of triethyl phosphite to obtain 49.3 g of a reaction product as a distillation residue. This was recrystallized from hexane to obtain 29.9 g of diethyl 3,3-di(p-tolyl)allylphosphite (7c).

Theoretical yield; 61.16%
M.p.; 56.0° C.
MS; 358(M$^+$), 314, 221, 129
$^1$H-NMR (δ; ppm in CDCl$_3$); 1.30 (6H, t, J=7.1 Hz), 2.32 (3H, s), 2.39 (3H, s), 2.71 (2H, dd, J=7.9 Hz, J=22.4 Hz), 4.07 (4H, q, J=7.1 Hz, J=8.1 Hz), 6.05 (1H, dd, J=7.9 Hz, J=15.2 Hz), 7.06–7.19 (8H, m)

(6) 3,6-Bis(4',4'-di-p-tolylbutadienyl)-9-benzylcarbazole (Exemplified Compound 25)

1.15 g (3.67 mmol) of 3,6-diformyl-9-benzylcarbazole (2d), 2.89 g (8.06 mmol) of diethyl 3,3-di-p-tolylallylphosphite, 20 ml of DMF and 1.0 g (8.91 mmol) of potassium-t-butoxide were allowed to react and after treated in the same manner as with Example 1 (2) to obtain 1.69 g of exemplified compound 25.

Yield; 63.8%, m.p.; 235°–236° C.
MS; 721(M$^+$), 195, 69, 43
$^1$H-NMR (δ; ppm in CDCl$_3$); 2.35 (s, 6H), 2.45 (s, 6H), 5.44 (s, 2H), 6.83–6.93 (m, 6H), 7.06–7.13 (m, 6H), 7.18–7.28 (m, 17H), 7.42 (d, J=8.6 Hz, 2H), 8.00 (s, 2H)

EXAMPLE 12

Synthesis of 3,6-Bis(2",2'-diphenylvinyl)-9-s-butylcarbazole (Exemplified Compound 26, m=n=0, Ar$^1$=R$^1$=Ar$^2$=R$^2$=Ph, R$^3$=a s-butyl group)

(1) 9-s-Butylcarbazole (4f)

30 g (179.46 mmol) of carbazole, 71 g of 85% KOH, 40 g of potassium carbonate, 6.0 g of tetra-n-butylammonium hydrogensulfate, 50.0 g (271.7 mmol) of 2-iodobutane and 300 ml of DMF were allowed to react and after treated in the same manner as with Example 7 (1) to obtain 9.66 g of 9-s-butylcarbazole.

Yield; 24.1%, m.p.; 62°–63° C.
MS; 223(M$^+$), 208, 194, 180, 167
$^1$H-NMR (δ; ppm in CDCl$_3$); 0.80 (t, J=7.4 Hz, 3H), 1.70 (d, J=7.0 Hz, 3H), 2.02 (m, 1H), 2.30 (m, 1H), 4.69 (m, 1H), 7.21 (t, J=7.8 Hz, 2H), 7.42 (t, J=8.3 Hz, 2H), 7.51 (d, J=8.2 Hz, 2H), 8.11 (d, J=7.7 Hz, 2H)

(2) 3,6-Diformyl-9-s-butylcarbazole (2f)

9.0 g (40.3 mmol) of 9-s-butylcarbazole, 17.9 g (245.4 mmol) of DMF, 6.0 g (44 mmol) of zinc chloride, 25.0 g (163.0 mmol) of phosphorus oxychloride and 75 ml of toluene were allowed to react and after treated in the same manner as with Example 1 (1) to obtain 5.07 g of 3,6-diformyl-9-s-butylcarbazole (2f).

Yield; 45.0%, m.p.; 176°–177° C.

MS; 279(M$^+$), 250, 222, 194, 167
$^1$H-NMR (δ; ppm in CDCl$_3$); 0.80 (t, J=7.4 Hz, 3H), 2.75 (d, J=7.0 Hz, 3H), 2.09 (m, 1H), 2.30 (m, 1H), 4.78 (m, 1H), 7.65 (t, J=8.7 Hz, 2H), 8.05 (d, J=8.6 Hz, 2H), 8.70 (s, 2H), 10.13 (s, 2H)

(3) 3,6-Bis(2',2'-diphenylvinyl)-9-s-butylcarbazole (Exemplified Compound 26)

1.80 g (6.44 mmol) of 3,6-diformyl-9-s-butylcarbazole (2f), 4.60 g (14.22 mmol) of diethyl diphenylmethylphosphite, 20 ml of DMF and 1.7 g (15.154 mmol) of potassium-t-butoxide were allowed to react and after treated in the same manner as with Example 1 (2) to obtain 2.93 g of exemplified compound 26.

Yield; 78.6%, m.p.; 100°–103° C.
MS; 579(M$^+$), 550, 523, 179
$^1$H-NMR (δ; ppm in CDCl$_3$); 0.75 (t, J=7.4 Hz, 3H), 1.58 (d, J=7.0 Hz, 2H), 1.90 (m, 1H), 2.15 (m, 1H), 4.48 (m, 1H), 7.13 (dd, J=8.8 Hz, J=1.8 Hz, 2H), 7.12 (s, 2H), 7.16 (d, J=8.6 Hz, 2H), 7.25–7.40 (m, 20H), 7.52 (d, J=1.7 Hz, 2H)

EXAMPLE 13

Synthesis of 3,6-Bis(4',4'-diphenylbutadienyl)-9-s-butylcarbazole (Exemplified Compound 27, m=n=1, Ar$^1$=R$^1$=Ar$^2$=R$^2$=Ph, R$^3$=a s-butyl group)

1.51 g (5.41 mmol) of 3,6-diformyl-9-s-butylcarbazole (2f), 3.93 g (11.9 mmol) of diethyl 3,3-diphenylallylphosphite, 20 ml of DMF and 1.4 g (12.5 mmol) of potassium-t-butoxide were allowed to react and after treated in the same manner as with Example 1 (2) to obtain 1.77 g of exemplified compound 27.

Yield; 51.8%, m.p.; 219°–220° C.
MS; 631(M$^+$), 602, 440, 412, 382, 816, 205, 167
$^1$H-NMR (δ; ppm in CDCl$_3$); 0.75 (t, J=7.3 Hz, 3H), 1.65 (d, J=7.0 Hz, 3H), 1.95 (m, 1H), 2.20 (m, 1H), 4.59 (m, 1H), 6.90 (m, 6H), 7.22–7.38 (m, 16H), 7.38–7.49 (m, 8H), 7.98 (d, J=1.5 Hz, 2H)

SYNTHESIS EXAMPLE 1

Synthesis of 4,4'-Bis(2",2"-diphenylvinylphenyl) methylamine (Comparative Compound 1)

3.0 g (12.5 mmol) of methyl-di-(p-formylphenyl)amine, 9.5 g (29.4 mmol) of diethyl diphenylmethylphosphite, 50 ml of DMF and 3.4 g (30.3 mmol) of potassium-t-butoxide were allowed to react and after treated in the same manner as with Example 1 (2) to obtain 5.05 g of comparative compound 1.

Yield; 74.9%, m.p.; 169°–170° C.

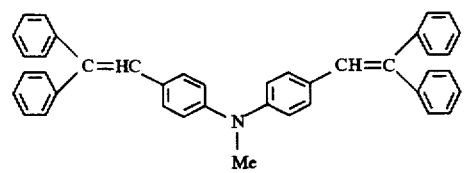

Comparative Compound 1

SYNTHESIS EXAMPLE 2

Synthesis of 3-(2',2'-Diphenylvinyl)-9-ethylcarbazole (Comparative Compound 2)

3-(2',2'-Diphenylvinyl)-9-ethylcarbazole synthesized in Example 2 (1) was used as comparative compound 2.

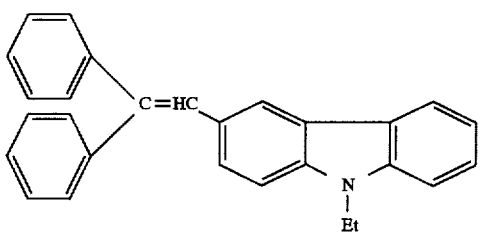

Comparative Compound 2

SYNTHESIS EXAMPLE 3

Synthesis of 3-(2',2'-Diphenylvinyl)-9-p-tolylcarbazole (Comparative Compound 3)

17.0 g (59.58 mmol) of 3-formyl-9-p-tolylcarbazole, 21.13 g (65.54 mmol) of diethyl diphenylmethylphosphite, 170 ml of DMF and 8.02 g (71.47 mmol) of potassium-t-butoxide were allowed to react and after treated in the same manner as with Example 1 (2) to obtain 21.56 g of comparative compound 3.

Yield: 83.0%, m.p.: 119°–120° C.

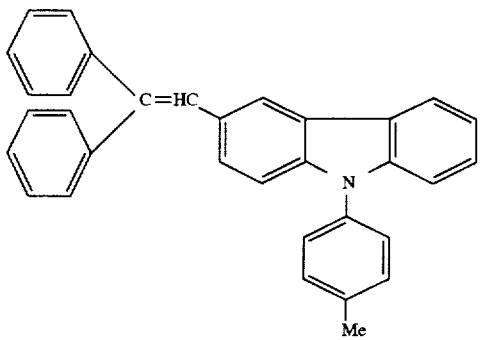

Comparative Compound 3

SYNTHESIS EXAMPLE 4

Synthesis of 3,6-Bis(2'-phenylvinyl)-9-phenylcarbazole (Comparative Compound 4)

2.0 g (6.68 mmol) of 3,6-diformyl-9-phenylcarbazole, 3.5 g (15.34 mmol) of diethyl benzylphosphite, 20 ml of DMF and 2.0 g (17.82 mmol) of potassium-t-butoxide were allowed to react and after treated in the same manner as with Example 1 (2) to obtain 2.20 g of comparative compound 4.

Yield: 73.6%, m.p.: 157°–158° C.

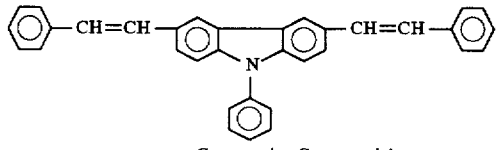

Comparative Compound 4

APPLICATION EXAMPLES 1 TO 4

One part of chlorodian blue (CDB) and one part of a polycarbonate resin (Yupilon E-2000 manufactured by Mitsubishi Gas Chemical Company, Inc.) were kneaded in a ball mill for 5 hours, using 30 parts of dichloroethane as a solvent. The resulting pigment dispersion was applied by use of a wire bar onto a sheet in which aluminum was vapor deposited over a polyethylene terephthalate (PET) film, and dried at 45° C. for 3 hours to form a charge carrier generating layer to a thickness of about 1 μm. Further, one part of each of exemplified compounds 4, 6, 16 and 21 and one part of a polycarbonate resin (Polycarbonate Z manufactured by Mitsubishi Gas Chemical Company, Inc.) were dissolved in 8 parts of dichloroethane by mixing. This solution was applied onto the charge carrier generating layer with a doctor blade, and dried at 80° C. for 3 hours. Thus, photoreceptors 1 to 4 were prepared.

The electrophotographic characteristics of the electrophotographic photoreceptors thus obtained were measured by the static system using an Electrostatic Paper Analyser Type SP-428 (manufactured by Kawaguchi Electric Works). That is, the photoreceptors were exposed to the corona discharge of −6 kV for 5 seconds to charge them, and the surface potential $V_0$ (unit: −V) was measured. They were kept in the dark for 5 seconds, followed by irradiation of light of 5 luxes with a tungsten lamp. Then, the exposure necessary for decaying the surface potential by half, namely the half-decay exposure $E_{1/2}$ (lux·second), and the surface residual potential $V_{R10}$ (−V) after irradiation of light having an illuminance of 5 luxes were determined. Results thereof are shown in Table 3.

COMPARATIVE EXAMPLES 1 TO 3

Photoreceptors 5 to 7 were prepared in the same manner as with Application Example 1 with the exception that comparative compounds 1 to 3 synthesized in Synthesis Examples 1 to 3 were used in place of exemplified compounds 4, 6, 16 and 21, and the electrophotographic characteristics thereof were measured. Results thereof are shown in Table 3.

APPLICATION EXAMPLES 5 TO 7

Oxotitanium phthalocyanine (TiOPc) was vacuum deposited at $10^{-6}$ Torr to a thickness of about 0.8 μm on an aluminum thin film deposited on a polyester film to form a charge carrier generating layer. Further, one part of each of exemplified compounds 14, 16 and 21 and one part of a polycarbonate resin (Polycarbonate Z manufactured by Mitsubishi Gas Chemical Company, Inc.) were dissolved in 8 parts of dichloroethane by mixing. This solution was applied onto the charge carrier generating layer with a doctor blade, and dried at 80° C. for 3 hours. Thus, photoreceptors 8 to 10 were prepared. The electrophotographic characteristics thereof were measured in the same manner as with Application Example 1. Results thereof are shown in Table 4.

COMPARATIVE EXAMPLES 4 TO 7

Photoreceptors 11 to 14 were prepared in the same manner as with Application Example 5 with the exception that comparative compounds 1 to 4 were used in place of comparative compound 14 used in Application Example 5, and the electrophotographic characteristics thereof were measured. Results thereof are shown in Table 4.

As apparent from Tables 3 and 4, it is shown that the compounds of the present invention have low value in the half-decay exposure $E_{1/2}$ (good in sensitivity), and are low in residual potential, compared with the comparative compounds. In Comparative Examples 2 and 3, even irradiation of light having an illuminance of 5 luxes several seconds could not decay the surface potential by half, resulting in failure to measure the value of the half-decay exposure $E_{1/2}$.

APPLICATION EXAMPLES 8 TO 13

One part of each of exemplified compounds 4, 5, 14, 16, 21 and 26 and one part of a polycarbonate resin were dissolved in 8 parts of dichloroethane by mixing. This solution was applied with a doctor blade onto a sheet in which aluminum was deposited over a polyethylene terephthalate (PET) film, and dried at 80° C. for 2 hours. Thus, photoreceptors 15 to 20 were prepared. Further, a translucent gold electrode was deposited over a charge transporting layer, and the charge carrier mobility was measured. The measurement of the carrier mobility was made by the time-of-flight method (Toshiaki Tanaka, Yasuhiro Yamaguchi and Masaaki Yokoyama, *Denshi Shashin* (*Electrophotography*), 29, 366 (1990)) using a nitrogen gas laser having a pulse half width of 0.9 nsec. and a wavelength of 337 nm as a light source. Results measured at 25° C. at 25 V/um are shown in Table 5.

COMPARATIVE EXAMPLE 8

Photoreceptor 21 was prepared in the same manner as with Application Example 8 with the exception that comparative compound 2 was used in place of exemplified compound 4, and the carrier mobility was measured. Results thereof are shown in Table 5.

TABLE 5

| Photoreceptor No. | | | Carrier Mobility μ ($cm^2 \cdot V^{-1} \cdot s^{-1}$) |
|---|---|---|---|
| Application Example 8 | 15 | Exemplified compound 4 | $17.1 \times 10^{-6}$ |
| Application Example 9 | 16 | Exemplified compound 5 | $11.4 \times 10^{-6}$ |
| Application Example 10 | 17 | Exemplified compound 14 | $18.5 \times 10^{-6}$ |
| Application Example 11 | 18 | Exemplified compound 16 | $12.3 \times 10^{-6}$ |
| Application Example 12 | 19 | Exemplified compound 21 | $42.4 \times 10^{-6}$ |
| Application Example 13 | 20 | Exemplified compound 26 | $13.0 \times 10^{-6}$ |
| Comparative Example 8 | 21 | Comparative comcompound 2 | $3.4 \times 10^{-6}$ |

As apparent from Table 5, the compounds of the present invention shows high carrier mobility, compared with the comparative example.

TABLE 3

| Photoreceptor No. | | Charge Generating Material | Charge Transporting Material | $V_0$ (—V) | $V_{R10}$ (—V) | $E_{1/2}$ (lux · sec) |
|---|---|---|---|---|---|---|
| Application Example 1 | 1 | CDB | Exemplified compound 4 | 1466 | 314 | 18.0 |
| Application Example 2 | 2 | CDB | Exemplified compound 6 | 1447 | 287 | 16.4 |
| Application Example 3 | 3 | CDB | Exemplified compound 16 | 1191 | 33 | 7.4 |
| Application Example 4 | 4 | CDB | Exemplified compound 21 | 1275 | 59 | 14.2 |
| Comparative Example 1 | 5 | CDB | Comparative compound 1 | 1356 | 468 | 23.0 |
| Comparative Example 2 | 6 | CDB | Comparative compound 2 | 1461 | 697 | Unmeasurable |
| Comparative Example 3 | 7 | CDB | Comparative compound 3 | 1459 | 790 | Unmeasurable |

TABLE 4

| Photoreceptor No. | | Charge Generating Material | Charge Transporting Material | $V_0$ (—V) | $V_{R10}$ (—V) | $E_{1/2}$ (lux · sec) |
|---|---|---|---|---|---|---|
| Application Example 5 | 8 | TiOPc deposition | Exemplified compound 14 | 1093 | 47 | 0.8 |
| Application Example 6 | 9 | TiOPc deposition | Exemplified compound 16 | 918 | 0 | 0.8 |
| Application Example 7 | 10 | TiOPc deposition | Exemplified compound 21 | 879 | 83 | 1.0 |
| Comparative Example 4 | 11 | TiOPc deposition | Comparative compound 1 | 1212 | 248 | 5.2 |
| Comparative Example 5 | 12 | TiOPc deposition | Comparative compound 2 | 1440 | 299 | 2.7 |
| Comparative Example 6 | 13 | TiOPc deposition | Comparative compound 3 | 1342 | 343 | 8.8 |
| Comparative Example 7 | 14 | TiOPc deposition | Comparative compound 4 | 1462 | 103 | 1.6 |

APPLICATION EXAMPLES 14 AND 15

One part by weight of τ-form metal-free phthalocyanine (τ-$H_2$Pc) and one part by weight of a butyral resin (Polyvinyl Butyral BM-1 manufactured by Sekisui Chemical Co., Ltd.) were kneaded in a ball mill for 5 hours, using 30 parts by weight of tetrahydrofuran as a solvent. The resulting pigment dispersion was applied onto a sheet in which aluminum was deposited over a polyethylene terephthalate (PET) film, and dried at 50° C. for 2 hours. Further, one part of each of exemplified compounds 16 and 26 and one part of a polycarbonate resin (Polycarbonate Z manufactured by Mitsubishi Gas Chemical Company, Inc.) were dissolved in 8 parts by weight of dichloroethane by mixing. This solution was applied onto a charge generating layer with a doctor blade, and dried at 80° C. for 2 hours. Thus, photoreceptors 22 and 23 were prepared. The electrophotographic characteristics of the photoreceptors thus obtained were measured in the same manner as with Application Example 1. Results thereof are shown in Table 6.

APPLICATION EXAMPLE 16

One part by weight of χ-form metal-free phthalocyanine (χ-H$_2$Pc) and one part by weight of a butyral resin (Polyvinyl Butyral BM-1 manufactured by Sekisui Chemical Co., Ltd.) were kneaded in a ball mill for 5 hours, using 30 parts by weight of tetrahydrofuran as a solvent. The

APPLICATION EXAMPLE 20

In the same manner as with Application Example 1, a charge generating layer was formed using chlorodian blue. As a charge transporting material, one part by weight of exemplified compound 16 and one part by weight of a bisphenol A/biphenol copolymerized polycarbonate resin (manufactured by Idemitsu Kosan Co., Ltd.) represented by the following structural formula in place of the polycarbonate resin (Polycarbonate Z manufactured by Mitsubishi Gas Chemical Company, Inc.) used in Application Examples 1 to 19 were dissolved in 8 parts by weight of dichloroethane by mixing. This solution was applied onto the charge generating layer of chlorodian blue with a doctor blade, and dried at 80° C. for 3 hours to prepare photoreceptor 28. The electrophotographic characteristics were evaluated in the same manner as with Application Example 1. Results thereof are shown in Table 7.

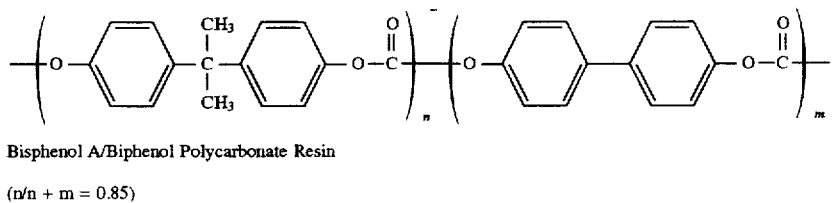

Bisphenol A/Biphenol Polycarbonate Resin (n/n + m = 0.85)

resulting pigment dispersion was applied onto a sheet in which aluminum was deposited over a polyethylene terephthatate (PET) film, and dried at 50° C. for 2 hours. Further, one part of exemplified compound 16 and one part of a polycarbonate resin (Polycarbonate Z manufactured by Mitsubishi Gas Chemical Company, Inc.) were dissolved in 8 parts by weight of dichloroethane by mixing. This solution was applied onto a charge generating layer with a doctor blade, and dried at 80° C. for 2 hours to prepare photoreceptor 24. The electrophotographic characteristics of the photoreceptor thus obtained were measured in the same manner as with Application Example 1. Results thereof are shown in Table 6.

APPLICATION EXAMPLES 17 TO 19

According to the method described in JP-A-1-291256, 40 parts by weight of crystalline oxytitanyl phthalocyanine was added to a binder resin solution obtained by dissolving 35 parts by weight of a butyral resin (Polyvinyl Butyral BM-1 manufactured by Sekisui Chemical Co., Ltd.) in 1425 parts by weight of tetrahydrofuran, and dispersed together with glass beads by use of a vibrating mill for 2 hours. This dispersion was applied onto a sheet in which aluminum was deposited over a polyethylene terephthalate (PET) film, and dried at 50° C. for 2 hours to form a charge generating layer having a thickness of about 0.5 μm. Further, one part by weight of each of exemplified compounds 14, 16 and 26 and one part by weight of a polycarbonate resin (Polycarbonate Z manufactured by Mitsubishi Gas Chemical Company, Inc.) were dissolved in 8 parts by weight of dichloroethane by mixing. This solution was applied onto the charge generating layer with a doctor blade, and dried at 80° C. for 2 hours. Thus, photoreceptors 25, 26 and 27 were prepared. The electrophotographic characteristics of the photoreceptors thus obtained were measured in-the same manner as with Application Example 1. Results thereof are shown in Table 6.

APPLICATION EXAMPLE 21

In the same manner as with Application Example 5, oxotitanyl phthalocyanine (TiOPc) was vacuum deposited to form a charge generating layer. As a charge transporting material, one part by weight of exemplified compound 26 and one part by weight of the bisphenol A/biphenol copolymerized polycarbonate resin (manufactured by Idemitsu Kosan Co., Ltd.) used in Application Example 20 in place of the polycarbonate resin (Polycarbonate Z manufactured by Mitsubishi Gas Chemical Company, Inc.) used in Application Examples 1 to 19 were dissolved in 8 parts by weight of dichloroethane by mixing. This solution was applied onto the charge generating layer of oxotitanyl phthalocyanine (TiOPc) with a doctor blade, and dried at 80° C. for 3 hours to prepare photoreceptor 22. The electrophotographic characteristics were evaluated in the same manner as with Application Example 1. Results thereof are shown in Table 7.

APPLICATION EXAMPLE 22

In the same manner as with Application Example 14, a charge generating layer was prepared using τ-form metal-free phthalocyanine (τ-H$_2$Pc). As a charge transporting material, one part by weight of exemplified compound 14 and one part by weight of the bisphenol A/biphenol copolymerized polycarbonate resin (manufactured by Idemitsu Kosan Co., Ltd.) used in Application Example 20 in place of the polycarbonate resin (Polycarbonate Z manufactured by Mitsubishi Gas Chemical Company, Inc.) used in Application Examples 1 to 19 were dissolved in 8 parts by weight of dichloroethane by mixing. This solution was applied onto the charge generating layer of τ-form metal-free phthalocyanine (τ-H$_2$Pc) with a doctor blade, and dried at 80° C. for 3 hours to prepare photoreceptor 30. The electrophotographic characteristics were evaluated in the same manner as with Application Example 1. Results thereof are shown in Table 7.

APPLICATION EXAMPLES 23 TO 25

In the same manner as with Application Example 17, a charge generating layer is formed using crystalline oxytitanyl phthalocyanine (TiOPc crystal). As a charge transporting material, one part by weight of each of exemplified compounds 14, 16 and 26 and one part by weight of the bisphenol A/biphenol copolymerized polycarbonate resin (manufactured by Idemitsu Kosan. Co., Ltd.) used in Application Example 20 in place of the polycarbonate resin (Polycarbonate Z manufactured by Mitsubishi Gas Chemical Company, Inc.) used in Application Examples 1 to 19 were dissolved in 8 parts by weight of dichloroethane by mixing. This solution was applied onto the charge generating layer of crystalline oxytitanyl phthalocyanine (TiOPc crystal) with a doctor blade, and dried at 80° C. for 3 hours. Thus, photoreceptors 31, 32 and 33 were prepared. The electrophotographic characteristics were evaluated in the same manner as with Application Example 1. Results thereof are shown in Table 7.

APPLICATION EXAMPLES 26 TO 28

0.5 part by weight of exemplified compound 14 and 0.5 part by weight of hydrazone compound (I-1) represented by the following structural formula were dissolved in 8 parts by weight of dichloroethane together with one part by weight of the polycarbonate resin (Polycarbonate Z manufactured by Mitsubishi Gas Chemical Company, Inc.). This charge transporting material solution was applied with a doctor blade onto a charge generating layer using CDB formed in the same manner as with Application Example 1, and dried at 80° C. for 3 hours to prepare photoreceptor 34. Further, this charge transporting material solution was applied with a doctor blade onto a charge generating layer using vacuum-deposited oxotitanium phthalocyanine (TiOPc deposition) formed in the same manner as with Application Example 5, and dried at 80° C. for 3 hours to prepare photoreceptor 35. Furthermore, this charge transporting material solution was applied with a doctor blade onto a charge generating layer using crystalline oxytitanyl phthalocyanine (crystalline TiOPc) formed in the same manner as with Application Example 17, and dried at 80° C. for 3 hours to prepare photoreceptor 36. For photoreceptors 34, 35 and 36, the electrophotographic characteristics were evaluated in the same manner as with Application Example 1. Results thereof are shown in Table 8.

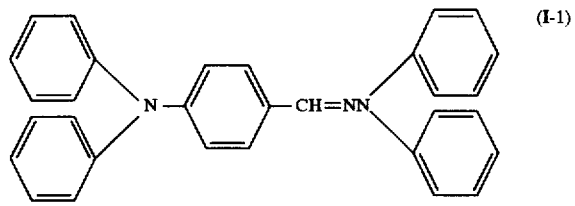

APPLICATION EXAMPLES 29 AND 30

0.2 part by weight of exemplified compound 16 and 0.8 part by weight of hydrazone compound (I-2) represented by the following structural formula were dissolved in 8 parts by weight of dichloroethane together with one part by weight of the bisphenol A/biphenol copolymerized polycarbonate resin (manufactured by Idemitsu Kosan Co., Ltd.) used in Application Example 20. This charge transporting material solution was applied with a doctor blade onto a charge generating layer using CDB formed in the same manner as with Application Example 1, and dried at 80° C. for 3 hours to prepare photoreceptor 37. Further, this charge transporting material solution was applied with a doctor blade onto a charge generating layer using vacuum-deposited oxotitanium phthalocyanine (TiOPc deposition) formed in the same manner as with Application Example 5, and dried at 80° C. for 3 hours to prepare photoreceptor 38. For photoreceptors 37 and 38, the electrophotographic characteristics were evaluated in the same manner as with Application Example 1. Results thereof are shown in Table 8.

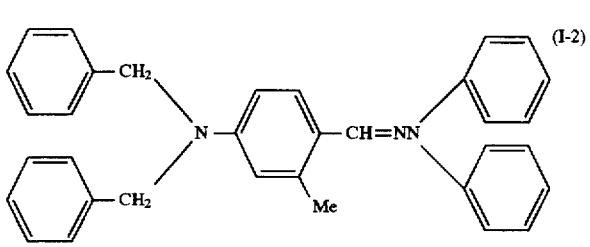

APPLICATION EXAMPLES 31 TO 33

0.5 part by weight of exemplified compound 16 and 0.5 part by weight of triphenylamine dimer compound (II-1) represented by the following structural formula were dissolved in 8 parts by weight of dichloroethane together with one part by weight of the polycarbonate resin (Polycarbonate Z manufactured by Mitsubishi Gas Chemical Company, Inc.). This charge transporting material solution was applied with a doctor blade onto a charge generating layer using vacuum-deposited oxotitanium phthalocyanine (TiOPc deposition) formed in the same manner as with Application Example 5, and dried at 80° C. for 3 hours to prepare photoreceptor 39. Further, this charge transporting material solution was applied with a doctor blade onto a charge generating layer using τ-form metal-free phthalocyanine (τ-$H_2$Pc) formed in the same manner as with Application Example 14, and dried at 80° C. for 3 hours to prepare photoreceptor 40. Furthermore, this charge transporting material solution was applied with a doctor blade onto a charge generating layer using χ-form metal-free phthalocyanine (χ-$H_2$Pc) formed in the same manner as with Application Example 16, and dried at 80° C. for 3 hours to prepare photoreceptor 41. For photoreceptors 39, 40 and 41, the electrophotographic characteristics were evaluated in the same manner as with Application Example 1. Results thereof are shown in Table 9.

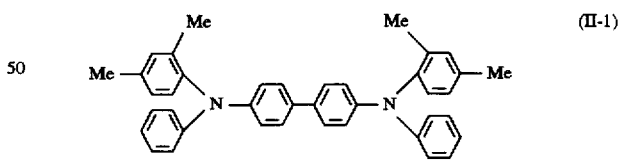

APPLICATION EXAMPLES 34 TO 36

0.4 part by weight of exemplified compound 26 and 0.6 part by weight of triphenylamine dimer compound (II-2) represented by the following structural formula were dissolved in 8 parts by weight of dichloroethane together with one part by weight of the polycarbonate resin (Polycarbonate Z manufactured by Mitsubishi Gas Chemical Company, Inc.). This charge transporting material solution was applied with a doctor blade onto a charge generating layer using vacuum-deposited oxotitanium phthalocyanine (TiOPc deposition) formed in the same manner as with Application Example 5, and dried at 80° C.

for 3 hours to prepare photoreceptor 42. Further, this charge transporting material solution was applied with a doctor blade onto a charge generating layer using τ-form metal-free phthalocyanine (τ-H₂Pc) formed in the same manner as with Application Example 14, and dried at 80° C. for 3 hours to prepare photoreceptor 43. Furthermore, this charge transporting material solution was applied with a doctor blade onto a charge generating layer using χ-form metal-free phthalocyanine (χ-H₂Pc) formed in the same manner as with Application Example 16, and dried at 80° C. for 3 hours to prepare photoreceptor 44. For photoreceptors 42, 43 and 44, the electrophotographic characteristics were evaluated in the same manner as with Application Example 1. Results thereof are shown in Table 9.

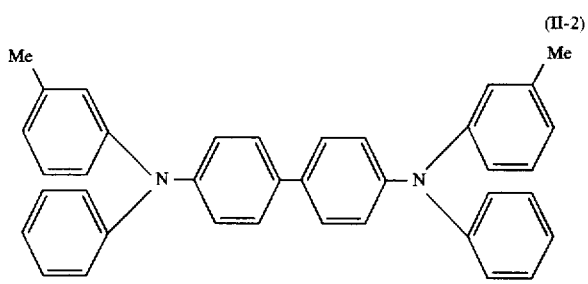

(II-2)

APPLICATION EXAMPLES 37 TO 39

0.3 part by weight of exemplified compound 14 and one part by weight of distyryl compound (III-1) represented by the following structural formula were dissolved in 8 parts by weight of dichloroethane together with one part by weight of the bisphenol A/biphenol copolymerized polycarbonate resin (manufactured by Idemitsu Kosan Co., Ltd.) used in Application Example 20. This charge transporting material solution was applied with a doctor blade onto a charge generating layer using vacuum-deposited oxotitanium phthalocyanine (TiOPc deposition) formed in the same manner as with Application Example 5, and dried at 80° C. for 3 hours to prepare photoreceptor 45. Further, this charge transporting material solution was applied with a doctor blade onto a charge generating layer τ-form metal-free phthalocyanine (τ-H2Pc) formed in the same manner as with Application Example 14, and dried at 80° C. for 3 hours to prepare photoreceptor 46. Furthermore, this charge transporting material solution was applied with a doctor blade onto a charge generating layer using crystalline oxytitanyl phthalocyanine (crystalline TiOPc) formed in the same manner as with Application Example 17, and dried at 80° C. for 3 hours to prepare photoreceptor 47. For photoreceptors 45, 46 and 47, the electrophotographic characteristics were evaluated in the same manner as with Application Example 1. Results thereof are shown in Table 10.

APPLICATION EXAMPLES 40 AND 41

0.5 part by weight of exemplified compound 26 and 0.5 part by weight of distyryl compound (III-1) were dissolved in 8 parts by weight of dichloroethane together with one part by weight of the bisphenol A/biphenol copolymerized polycarbonate resin (manufactured by Idemitsu Kosan Co., Ltd.) used in Application Example 20. This charge transporting material solution was applied with a doctor blade onto a charge generating layer using vacuum-deposited oxotitanium phthalocyanine (TiOPc deposition) formed in the same manner as with Application Example 5, and dried at 80° C. for 3 hours to prepare photoreceptor 48. Further, this charge transporting material solution was applied with a doctor blade onto a charge generating layer using crystalline oxytitanyl phthalocyanine (crystalline TiOPc) formed in the same manner as with Application Example 17, and dried at 80° C. for 3 hours to prepare photoreceptor 49. For photoreceptors 48 and 49, the electrophotographic characteristics were evaluated in the same manner as with Application Example 1. Results thereof are shown in Table 10. As indicated in Tables 6 to 10, even the use of the compounds of the present invention-in combination with other charge transporting materials exhibits good photoreceptive characteristics.

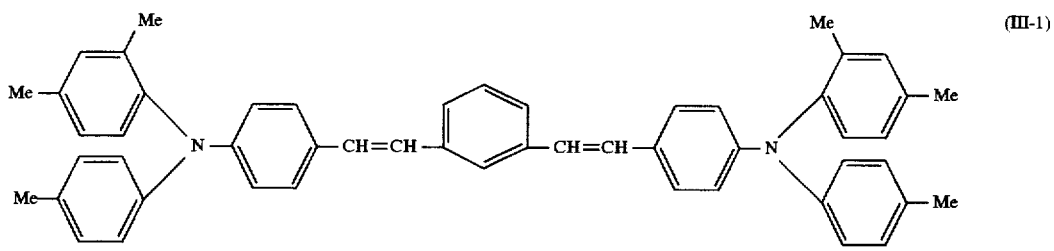

(III-1)

TABLE 6

| | Photoreceptor No. | Charge Generating Material | Charge Transporting Material | $V_0$ (—V) | $V_{R10}$ (—V) | $E_{1/2}$ (lux · sec) |
|---|---|---|---|---|---|---|
| Application Example 14 | 22 | τ-H$_2$Pc | Exemplified compound 16 | 871 | 0 | 0.9 |
| Application Example 15 | 23 | τ-H$_2$Pc | Exemplified compound 26 | 632 | 41 | 1.0 |
| Application Example 16 | 24 | χ-H$_2$Pc | Exemplified compound 16 | 837 | 0 | 1.0 |
| Application Example 17 | 25 | TiOPc crystal | Exemplified compound 14 | 746 | 1 | 0.4 |
| Application Example 18 | 26 | TiOPc crystal | Exemplified compound 16 | 690 | 0 | 0.3 |
| Application Example 19 | 27 | TiOPc crystal | Exemplified compound 26 | 745 | 9 | 0.4 |

TABLE 7

| | Photoreceptor No. | Charge Generating Material | Charge Transporting Material | $V_0$ (—V) | $V_{R10}$ (—V) | $E_{1/2}$ (lux · sec) |
|---|---|---|---|---|---|---|
| Application Example 20 | 28 | CDB | Exemplified compound 16 | 918 | 0 | 6.6 |
| Application Example 21 | 29 | TiOPc deposition | Exemplified compound 26 | 910 | 110 | 1.5 |
| Application Example 22 | 30 | τ-H$_2$Pc | Exemplified compound 14 | 761 | 55 | 1.2 |
| Application Example 23 | 31 | TiOPc crystal | Exemplified compound 14 | 646 | 6 | 0.4 |
| Application Example 24 | 32 | TiOPc crystal | Exemplified compound 16 | 520 | 0 | 0.4 |
| Application Example 25 | 33 | TiOPc crystal | Exemplified compound 26 | 703 | 1 | 0.4 |

TABLE 8

| | Photoreceptor No. | Charge Generating Material | Polymer Binder | Charge Transporting Material | $V_0$ (—V) | $V_{R10}$ (—V) | $E_{1/2}$ (lux · sec) |
|---|---|---|---|---|---|---|---|
| Application Example 26 | 34 | CDB | Polycarbonate Z | Exemplified compound 14 0.5 part by weight Compound (I-1) 0.5 part by weight | 1085 | 51 | 5.6 |
| Application Example 27 | 35 | TiOPc deposition | Polycarbonate Z | Exemplified compound 14 0.5 part by weight Compound (I-1) 0.5 part by weight | 984 | 31 | 0.7 |
| Application Example 28 | 36 | TiOPc crystal | Polycarbonate Z | Exemplified compound 14 0.5 part by weight Compound (I-1) 0.5 part by weight | 737 | 13 | 0.5 |
| Application Example 29 | 37 | CDB | Bisphenol A/biphenol copolymerized polycarbonate | Exemplified compound 16 0.2 part by weight Compound (I-2) 0.8 part by weight | 877 | 11 | 3.2 |
| Application Example 30 | 38 | TiOPc deposition | Bisphenol A/biphenol copolymerized polycarbonate | Exemplified compound 16 0.2 part by weight Compound (I-2) 0.8 part by weight | 1030 | 18 | 0.8 |

TABLE 9

| Photo-receptor No. | Charge Generating Material | Polymer Binder | Charge Transporting Material | $V_0$ (—V) | $V_{R10}$ (—V) | $E_{1:2}$ (lux · sec) |
|---|---|---|---|---|---|---|
| Application Example 31 | 39 | TiOPc deposition | Polycarbonate Z | Exemplified compound 16 0.5 part by weight Compound (II-1) 0.5 part by weight | 953 | 0 | 0.5 |
| Application Example 32 | 40 | τ-H$_2$PC | " | Exemplified compound 16 0.5 part by weight Compound (II-1) 0.5 part by weight | 535 | 0 | 0.7 |
| Application Example 33 | 41 | χ-H$_2$Pc | " | Exemplified compound 16 0.5 part by weight Compound (II-1) 0.5 part by weight | 813 | 0 | 0.8 |
| Application Example 34 | 42 | TiOPc deposition | " | Exemplified compound 26 0.4 part by weight Compound (II-2) 0.6 part by weight | 983 | 21 | 0.7 |
| Application Example 35 | 43 | τ-H$_2$PC | " | Exemplified compound 26 0.4 part by weight Compound (II-2) 0.6 part by weight | 535 | 9 | 1.1 |
| Application Example 36 | 44 | χ-H$_2$Pc | " | Exemplified compound 26 0.4 part by weight Compound (II-2) 0.6 part by weight | 867 | 4 | 1.0 |

TABLE 10

| Photo-receptor No. | Charge Generating Material | Polymer Binder | Charge Transporting Material | $V_0$ (—V) | $V_{R10}$ (—V) | $E_{1:2}$ (lux · sec) |
|---|---|---|---|---|---|---|
| Application Example 37 | 45 | TiOPc deposition | Bisphenol A/biphenol copolymerized polycarbonate | Exemplified compound 14 0.3 part by weight Compound (III-1) 0.7 part by weight | 1932 | 5 | 0.5 |
| Application Example 38 | 46 | τ-H$_2$PC | Bisphenol A/biphenol copolymerized polycarbonate | Exemplified compound 14 0.3 part by weight Compound (III-1) 0.7 part by weight | 712 | 3 | 0.8 |
| Application Example 39 | 47 | TiOPc crystal | Bisphenol A/biphenol copolymerized polycarbonate | Exemplified compound 14 0.3 part by weight Compound (III-1) 0.7 part by weight | 546 | 0 | 0.3 |
| Application Example 40 | 48 | TiOPc deposition | Bisphenol A/biphenol copolymerized polycarbonate | Exemplified compound 26 0.5 part by weight Compound (III-1) 0.5 part by weight | 1253 | 60 | 0.6 |
| Application Example 41 | 49 | TiOPc crystal | Bisphenol A/biphenol copolymerized polycarbonate | Exemplified compound 26 0.5 part by weight Compound (III-1) 0.5 part by weight | 884 | 7 | 0.4 |

As described above, the carbazole derivatives (1) of the present invention are high in solubility in the binder polymers at the time when the electrophotographic photoreceptors are prepared, and the photoreceptors using the derivatives can exhibit high carrier mobility, and moreover, are high in sensitivity and-low in residual potential. The derivatives are therefore industrially excellent compounds.

While the invention has been described in detail and with reference to specific embodiments thereof, it will be apparent to one skilled in the art that various changes and modifications can be made therein without departing from the spirit and scope thereof.

What is claimed is:

1. A carbazole derivative represented by the following general formula (1):

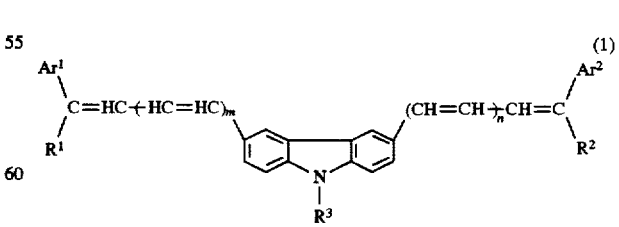

wherein $Ar^1$ and $Ar^2$, which may be the same or different, each represents an aryl group which may have a substituent group; $R^1$ and $R^2$, which may be the same or different, each represents a lower alkyl group-or an aryl group which may have a substituent group; $R^3$ represents a lower alkyl group, an alicyclic alkyl group having 5 to 7 carbon atoms, an aryl group which may have a substituent group, or an aralkyl group which may have a substituent group; and m and n each represents an integer of 0 or 1.

2. A charge transporting material containing a carbazole derivative represented by the following general formula (1):

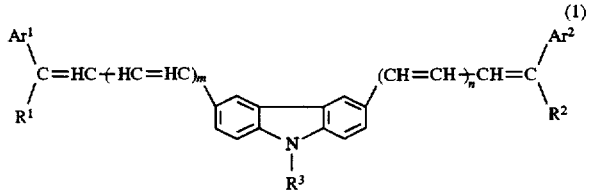

wherein $Ar^1$ and $Ar^2$, which may be the same or different, each represents an aryl group which may have a substituent group; $R^1$ and $R^2$, which may be the same or different, each represents a lower alkyl group or an aryl group which may have a substituent group; $R^3$ represents a lower alkyl group, an alicyclic alkyl group having 5 to 7 carbon atoms, an aryl group which may have a substituent group, or an aralkyl group which may have a substituent group; and m and n each represents an integer of 0 or 1.

3. An electrophotographic photoreceptor containing a charge transporting material containing a carbazole derivative represented by the following general formula (1):

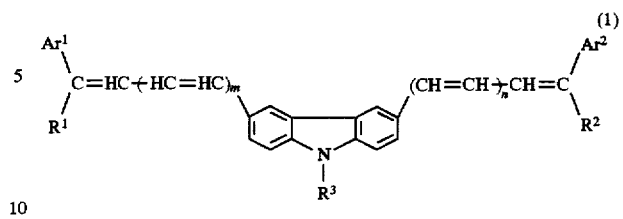

wherein $Ar^1$ and $Ar^2$, which may be the same or different, each represents an aryl group which may have a substituent group; $R^1$ and $R^2$, which may be the same or different, each represents a lower alkyl group or an aryl group which may have a substituent group; $R^3$ represents a lower alkyl group, an alicyclic alkyl group having 5 to 7 carbon atoms, an aryl group which may have a substituent group, or an aralkyl group which may have a substituent group; and m and n each represents an integer of 0 or 1.

* * * * *